(12) United States Patent
Widge et al.

(10) Patent No.: US 10,758,174 B2
(45) Date of Patent: Sep. 1, 2020

(54) METHOD FOR CROSS-DIAGNOSTIC IDENTIFICATION AND TREATMENT OF NEUROLOGIC FEATURES UNDERPINNING MENTAL AND EMOTIONAL DISORDERS

(71) Applicants: THE GENERAL HOSPITAL CORPORATION, Boston, MA (US); MASSACHUSETTS INSTITUTE OF TECHNOLOGY, Cambridge, MA (US)

(72) Inventors: Alik S. Widge, Somerville, MA (US); Thilo Deckersbach, Boston, MA (US); Darin Dougherty, Boston, MA (US); Emad Eskandar, Nahant, MA (US); Kristen Ellard, Boston, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/305,551

(22) PCT Filed: Apr. 22, 2015

(86) PCT No.: PCT/US2015/026995
§ 371 (c)(1),
(2) Date: Oct. 20, 2016

(87) PCT Pub. No.: WO2016/069058
PCT Pub. Date: May 6, 2016

(65) Prior Publication Data
US 2017/0042474 A1    Feb. 16, 2017

Related U.S. Application Data

(60) Provisional application No. 61/984,466, filed on Apr. 25, 2014, provisional application No. 61/984,416, filed on Apr. 25, 2014.

(51) Int. Cl.
*A61N 1/37* (2006.01)
*A61B 5/00* (2006.01)
(Continued)

(52) U.S. Cl.
CPC ............ *A61B 5/4836* (2013.01); *A61B 3/112* (2013.01); *A61B 3/113* (2013.01); *A61B 5/0008* (2013.01);
(Continued)

(58) Field of Classification Search
None
See application file for complete search history.

(56) References Cited

U.S. PATENT DOCUMENTS

| 5,392,788 A | 2/1995 | Hudspeth |
|---|---|---|
| 6,289,234 B1 | 9/2001 | Mueller |

(Continued)

FOREIGN PATENT DOCUMENTS

CN    103815901 A    5/2014

OTHER PUBLICATIONS

Schalk, et al., Two-Dimensional Movement Control Using Electrocorticographic Signals in Humans, J Neural Eng., 2008, 5(1):75-84.

(Continued)

*Primary Examiner* — Ankit D Tejani
(74) *Attorney, Agent, or Firm* — Quarles & Brady LLP

(57) ABSTRACT

A system and method for diagnosing mental or emotional disorders is disclosed. An affective BCI component is incorporated into a closed loop, symptom—responsive psychiatric DBS system. A series of input data related to a brain of the patient is acquired while the patient performs a battery of behavioral tasks. From the patient's performance on the task battery, the system identifies what is abnormal for that individual patient in terms of functional domains. Patient- (Continued)

specific behavioral measurements are then linked to patterns of activation and de-activation across different brain regions, identifying specific structures that are the source of the patient's individual impairment.

26 Claims, 16 Drawing Sheets

(51) Int. Cl.
    *A61N 1/378* (2006.01)
    *A61N 1/05* (2006.01)
    *A61N 1/36* (2006.01)
    *G16H 20/40* (2018.01)
    *G16H 20/70* (2018.01)
    *A61B 5/024* (2006.01)
    *A61B 5/053* (2006.01)
    *A61B 5/16* (2006.01)
    *G06F 3/01* (2006.01)
    *A61B 3/11* (2006.01)
    *A61B 3/113* (2006.01)
    *A61B 5/0205* (2006.01)
    *A61B 5/04* (2006.01)
    *A61B 5/0402* (2006.01)
    *A61B 5/0488* (2006.01)
    *A61B 6/03* (2006.01)
    *A61B 8/08* (2006.01)
    *A61B 5/055* (2006.01)
    *A61B 5/08* (2006.01)

(52) U.S. Cl.
    CPC ............ *A61B 5/0075* (2013.01); *A61B 5/024* (2013.01); *A61B 5/0205* (2013.01); *A61B 5/0402* (2013.01); *A61B 5/04008* (2013.01); *A61B 5/0488* (2013.01); *A61B 5/053* (2013.01); *A61B 5/165* (2013.01); *A61B 5/4064* (2013.01); *A61B 6/037* (2013.01); *A61B 8/0808* (2013.01); *A61N 1/0531* (2013.01); *A61N 1/0534* (2013.01); *A61N 1/36096* (2013.01); *A61N 1/36132* (2013.01); *A61N 1/36135* (2013.01); *A61N 1/36139* (2013.01); *A61N 1/3787* (2013.01); *G06F 3/015* (2013.01); *G16H 20/40* (2018.01); *G16H 20/70* (2018.01); *A61B 5/055* (2013.01); *A61B 5/0816* (2013.01)

(56) References Cited

U.S. PATENT DOCUMENTS

| | | | |
|---|---|---|---|
| 6,529,774 | B1 | 3/2003 | Greene |
| 6,539,263 | B1 | 3/2003 | Schiff et al. |
| 7,353,065 | B2 | 4/2008 | Morrell |
| 7,547,279 | B2 | 6/2009 | Kim et al. |
| 7,623,927 | B2 | 11/2009 | Rezai |
| 8,000,794 | B2 | 8/2011 | Lozano |
| 8,190,248 | B2 | 5/2012 | Besio et al. |
| 8,262,714 | B2 | 9/2012 | Hulvershorn et al. |
| 8,280,516 | B2 | 10/2012 | Graupe |
| 8,463,371 | B2 | 6/2013 | Guan et al. |
| 8,498,708 | B2 | 7/2013 | Bentwich |
| 8,690,748 | B1 | 4/2014 | Fu |
| 8,694,087 | B2 | 4/2014 | Schiff |
| 8,718,779 | B2 | 5/2014 | Whitehurst et al. |
| 8,762,065 | B2 | 6/2014 | DiLorenzo |
| 8,774,923 | B2 | 7/2014 | Rom |
| 8,838,247 | B2 | 9/2014 | Hagedorn et al. |
| 2003/0093129 | A1 | 5/2003 | Nicolelis et al. |
| 2004/0131998 | A1 | 7/2004 | Marom et al. |
| 2007/0156179 | A1 | 7/2007 | S.E. |
| 2008/0103547 | A1 | 5/2008 | Okun et al. |
| 2009/0105786 | A1 | 4/2009 | Fetz et al. |
| 2009/0118787 | A1 | 5/2009 | Moffitt et al. |
| 2009/0125079 | A1 | 5/2009 | Armstrong et al. |
| 2009/0157141 | A1 | 6/2009 | Chiao et al. |
| 2009/0306741 | A1 | 12/2009 | Hogle et al. |
| 2010/0036453 | A1 | 2/2010 | Hulvershorn et al. |
| 2011/0028827 | A1 | 2/2011 | Sitaram et al. |
| 2011/0130615 | A1 | 6/2011 | Mishelevich |
| 2011/0307029 | A1 | 12/2011 | Hargrove |
| 2011/0307079 | A1 | 12/2011 | Oweiss et al. |
| 2012/0108998 | A1 | 5/2012 | Molnar et al. |
| 2012/0150545 | A1 | 6/2012 | Simon |
| 2012/0310107 | A1* | 12/2012 | Doidge ................. A61B 5/048 600/545 |
| 2013/0138011 | A1 | 5/2013 | Ang et al. |
| 2013/0245424 | A1 | 9/2013 | deCharms |
| 2013/0281759 | A1* | 10/2013 | Hagedorn ............ A61B 5/0482 600/13 |
| 2014/0058189 | A1 | 2/2014 | Stubbeman |
| 2014/0074180 | A1 | 3/2014 | Heldman et al. |

OTHER PUBLICATIONS

Schlaepfer, et al., Rapid Effects of Deep Brain Stimulation for Treatment-Resistant Major Depression, Biological Psychiatry, 2013, 73(12):1204-1212.

Sitaram, et al., Real-Time Support Vector Classification and Feedback of Multiple Emotional Brain States, NeuroImage, 2011, 56(2):753-765.

Talwar, et al., Rat Navigation Guided by Remote Control, Nature, 2002, 417:37-38.

Vizueta, et al., Regional fMRI Hypoactivation and Altered Functional Connectivity During Emotion Processing in Nonmedicated Depressed Patients with Bipolar II Disorder, Am J Psychiatry, 2012, 169:831-840.

Ward, et al., Evolving Refractory Major Depressive Disorder Diagnostic and Treatment Paradigms: Toward Closed-Loop Therapeutics, Frontiers in Neuroengineering, 2010, vol. 3, Article 7, pp. 1-15.

Whiteford, et al., Global Burden of Disease Attributable to Mental and Substance Use Disorders: Findings from the Global Burden of Disease Study 2010, The Lancet, 2013, 382(9904):1575-1586.

Widge, et al., Baseline and Treatment-Emergent EEG Biomarkers of Antidepressant Medication Response Do Not Predict Response to Repetitive Transcranial Magnetic Stimulation, Brain Stimul, 2013, 6(6):929-931.

Widge, et al., Pre-Frontal Control of Closed-Loop Limbic Neurostimulation by Rodents Using a Brain-Computer Interface, Journal of Neural Engineering, 2014, 11(2):024001, 17 pages.

Widge, et al., Chapter 7—Direct Neural Control of Anatomically Correct Robotic Hands, Book: Brain-Computer Interfaces—Applying our Minds to Human-Computer Interaction, Copyright Springer-Verlag London Limited 2010, pp. 105-119.

Widge, et al., Psychosis from Subthalamic Nucleus Deep Brain Stimulator Lesion Effect, Surgical Neurology International, 2013, 4:7, 7 pages.

PCT International Search Report and Written Opinion, PCT/US2015/27042, dated Jul. 28, 2015, 13 pages.

PCT International Search Report and Written Opinion, PCT/US2015/26995, dated Nov. 27, 2015, 12 pages.

Afshar, et al., A Translational Platform for Prototyping Closed-Loop Neuromodulation Systems, Frontiers in Neural Circuits, 2013, vol. 6, Article 117, pp. 1-15.

Allison, et al., Toward Smarter BCIs: Extending BCIs: Through Hybridization and Intelligent Control, Journal of Neural Engineering, 2012, 9:013001, pp. 1-7.

Bewernick, et al., Long-Term Effects of Nucleus Accumbens Deep Brain Stimulation in Treatment-Resistant Depression: Evidence for Sustained Efficacy, Neuropsychopharmacology, 2012, 37:1975-1985.

Birbaumer, Breaking the Silence: Brain-Computer Interfaces (BCI) for Communication and Motor Control, Psychophysiology, 2006, 43:517-532.

(56) References Cited

OTHER PUBLICATIONS

Blakely, et al., Robust, Long-Term Control of an Electrocorticographic Brain-Computer Interface with Fixed Parameters, Neurosurg Focus, 2009, 27(1):E13, pp. 1-5.
Brouwer, et al., Effortless Passive BCIs for Healthy Users, UAHCI/HCII 2013, Part I, LNCS 8009, pp. 615-622.
Carlezon Jr., et al., Intracranial Self-Stimulation (ICSS) in Rodents to Study the Neurobiology of Motivation, Nature Protocols, 2007, 2:2987-2995.
Carmena, et al., Learning to Control a Brain-Machine Interface for Reaching and Grasping by Primates, PLoS Biology, 2003, 1(2):193-208.
Cromer, et al., Representation of Multiple, Independent Categories in the Primate Prefrontal Cortex, Neuron, 2010, 66:796-807.
Curran, et al., Learning to Control Brain Activity: A Review of the Production and Control of EEG Components for Drivng Brain-Computer Interface (BCI) Systems, Brain and Cognition, 2003, 51(3):326-336.
Cuthbert, et al., Toward the Future of Psychiatric Diagnosis: The Seven Pillars of RDoC, BMC Medicine, 2013, 11:126, 8 pages.
Ellard et al., Unified Protocol for the Transdiagnostic Treatment of Emotional Disorders: Protocol Development and Initial Outcome Data, Cognitive and Behavioral Practice, 2010, 17(1):88-101.
Etkin, et al., Resolving Emotional Conflict: A Role for the Rostral Anterior Cingulate Cortex in Modulating Activity in the Amygdala, Neuron, 2006, 51:871-882.
Etkin et al., Functional Neuroimaging of Anxiety: A Meta-Analysis of Emotional Processing in PTSD, Social Anxiety Disorder, and Specific Phobia, Am J Psychiatry, 2007, 164:1476-1488.
Felton, et al., Electrocorticographically Controlled Brain-Computer Interfaces Using Motor and Sensory Imagery in Patients with Temporary Subdural Electrode Implants, J Neurosurg, 2007, 106:495-500.
Foa, et al., Randomized, Placebo-Controlled Trial of Exposure and Ritual Prevention, Clomipramine, and Their Combination in the Treatment of Obsessive-Compulsive Disorder, Am J Psychiatry, 2005, 162:151-161.
Hamilton, et al., Functional Neuroimaging of Major Depressive Disorder: A Meta-Analysis and New Integration of Baseline Activation and Neural Response Data, Am J Psychiatry, 2012, 169:693-703.
Flint, et al., Accurate Decoding of Reaching Movements from Field Potentials in the Absence of Spikes, J Neural Eng, 2012, 9(4):046006, 22 pages.
Flint, et al., Long Term, Stable Brain Machine Interface Performance Using Local Field Potentials and Multiunit Spikes, J Neural Eng., 2013, 10(5):056005, 21 pages.
Gage, et al., Naive Coadaptive Cortical Control, Journal of Neural Engineering, 2005, 2:52-63.
Ganguly, et al., Reversible Large-Scale Modification of Cortical Networks During Neuroprosthetic Control, Nat Neurosci, 2011, 14(5):662-667.
Holtzheimer, et al., Subcallosal Cingulate Deep Brain Stimulation for Treatment-Resistant Unipolar and Bipolar Depression, Arch Gen Psychiatry, 2012, 69(2):150-158.
Ifft, et al., Brain-Machine Interface Enables Bimanual Arm Movements in Monkeys, Sci Transl Med, 2013, 5(210):210ra154, 29 pages.
Jackson, et al., Long-Term Motor Cortex Plasticity Induced by an Electronic Neural Implant, Nature, 2006, 444:56-60.
Kennedy, et al., Deep Brain Stimulation for Treatment-Resistant Depression: Follow-Up After 3 to 6 Years, Am J Psychiatry, 2011, 168:502-510.
Kim, et al., A Review on the Computational Methods for Emotional State Estimation from the Human EEG, Computational and Mathematical Methods in Medicine, 2013, vol. 2013, Article ID 573734, 13 pages.
Kim, et al., Point-and-Click Cursor Control With an Intracortical Neural Interface System by Humans With Tetraplegia, IEEE Trans Neural Syst Rehabil Eng, 2011, 19(2):193-203.
Koralek, et al., Cortiscostriatal Plasticity is Necessary for Learning Intentional Neuroprosthetic Skills, Nature, 2012, 483(7389):331-335.
Kothe, et al., Emotion Recognition from EEG During Self-Paced Emotional Imagery, In Proceedings of Affective Brain-Computer Interfaces (aBCI) Workshop, IEEE Affective Computing and Intelligent Interaction, 2013, 5 pages.
Kragel, et al., Multivariate Pattern Classification Reveals Autonomic and Experiential Representations of Discrete Emotions, Emotion, 2013, 13(4):681-690.
Lim, et al., Dopmaine Dysregulation Syndrome, Impulse Control Disorders and Punding After Deep Brain Stimulation Surgery for Parkinson's Disease, Journal of Clinical Neuroscience, 2009, 16(9):1148-1152.
Malone Jr., et al., Deep Brain Stimulation of the Ventral Capsule/Ventral Striatum for Treatment-Resistant Depression, Biol Psychiatry, 2009, 65(4):267-275.
Marzullo, et al., Suitability of the Cingulate Cortex for Neural Control, IEEE Transactions on Neural Systems and Rehabilitation Engineering, 2006, 14(4):401-409.
McLoughlin, et al., In Search of Biomarkers in Psychiatry: EEG-Based Measures of Brain Function, American Journal of Medical Genetics Part B: Neuropsychiatric Genetics, 2014, 165(2):111-121.
Mikhail, et al., Using Minimal Number of Electrodes for Emotion Detection Using Brain Signals Produced from a New Elicitation Technique, Int. J. Autonomous and Adaptive Communications Systems, 2013, 6(1):80-97.
Moghimi, et al., Automatic Detection of a Prefrontal Cortical Response to Emotionally Rated Music Using Multi-Channel Near-Infrared Spectroscopy, Journal of Neural Engineering, 2012, 9:026022, 8 pages.
Moritz, et al., Volitional Control of a Single Cortical Neurons in a Brain-Machine Interface, Journal of Neural Engineering, 2011, 8(2):025017, 15 pages.
Moritz, et al., Direct Control of Paralyzed Muscles by Cortical Neurons, Nature, 2008, 456(7222):639-642.
Morrell, et al., Responsive Cortical Stimulation for the Treatment of Medically Intractable Partial Epilepsy, Neurology, 2011, 77:1295-1304.
Nesse, et al., Towards a Genuinely Medical Model for Psychiatric Nosology, BMC Medicine, 2012, 10:5, 9 pages.
Nijboer, et al., Affective Brain-Computer Interfaces: Psychophysiological Markers of Emotion in Healthy Persons and in Persons with Amyotrophic Lateral Sclerosis, In 2009 Third International Conference on Affective Computing and Intelligent Interaction and Workshops, 2009, pp. 1-11.
Nijholt, et al., Editorial (to: Special Issue on Affective Brain-Computer Interfaces), International Journal of Autonomous and Adaptive Communications Systems, 2013, 6(1):1-8.
Nishimura, et al., Spike-Timing-Dependent Plasticity in Primate Corticospinal Connections Induced During Free Behavior, Neuron, 2013, 80:1301-1309.
Olds, Self-Stimulation of the Brain: Its Use to Study Local Effects of Hunger, Sex and Drugs, Science, 1958, 127(3294):315-324.
Pfurtscheller, et al. The Hybrid BCI, Frontiers in Neuroscience, 2010, vol. 4, Article 30, pp. 1-11.
Powers, et al., A Meta-Analytic Review of Prolonged Exposure for Posttraumatic Stress Disorder, Clinical Psychology Review, 2010, 30:635-641.
Price, Psychological and Neural Mechanisms of the Affective Dimension of Pain, Science, 2000, 288:1769-1772.
Price, et al., Neural Circuits Underlying the Pathophysiology of Mood Disorders, Trends in Cognitive Sciences, 2012, 16(1):61-71.
Rigotti, et al., The Importance of Mixed Selectivity in Complex Cognitive Tasks, Nature, 2013, 497(7451):585-590.
Sanchez, et al., Ascertaining the Importance of Neurons to Develop Better Brain-Machine Interfaces, IEEE Transactions on Biomedical Engineering, 2004, 51(6):943-953.

* cited by examiner

| Functional Domain | Self-Report Questionnaires (11 total) | Task | Disorders | | | | | | Brain Regions |
|---|---|---|---|---|---|---|---|---|---|
| Fear<br>- Fear Extinction<br>- Negative Affect<br>- Somatosensory | ASI*<br>ATQ*<br>STAI*<br>BIS/BAS* | Fear Extinction | PTSD | MDD | GAD | TBI | SUD | BPD Pain | vmPFC, sACC, amygdala, cg25, anterior insula, thalamus, periaqueductal gray |
| Reward Motivation<br>- Positive Affect<br>- Negative Affect<br>- Somatosensory | TEPS<br>BIS/BAS<br>PANAS<br>ATQ* | Aversion Reward Conflict (ARC) | PTSD | MDD | GAD | TBI | SUD | Pain | Ventral striatum, OFC |
| Emotion Regulation | DERS<br>ERS<br>ASI* | Emotion Conflict Resolution Task (ECR) | PTSD | MDD | GAD | TBI | SUD | BPD Pain | Amygdala, rACC, dlPFC |
| Decision Making / Impulsivity | BIS-11<br>ASRS<br>BRIEF**<br>ATQ* | Gambling Task (War Game) | | MDD | | TBI | SUD | BPD | OFC, subthalamic Nucleus |
| Attention / Perseveration | TRM<br>BRIEF**<br>ATQ* | Multi-Source Interference Task (MSIT) | PTSD | MDD | GAD | TBI | SUD | BPD | OFC, dlPFC, dACC |
| Cognition: - Learning / Memory | BRIEF* | Associative Learning Task | PTSD | MDD | GAD | TBI | SUD | | dlPFC, dACC, hippocampus, thalamus, dorsal striatum |
| Pre-Scan Measures | STAI*<br>PANAS** | | | | | | | | |

*Measures assess more than one functional domain.

FIG. 7

Behavior – recall deficit

METHOD FOR CROSS-DIAGNOSTIC IDENTIFICATION AND TREATMENT OF NEUROLOGIC FEATURES UNDERPINNING MENTAL AND EMOTIONAL DISORDERS

CROSS-REFERENCES TO RELATED APPLICATIONS

This application represents the U.S. National Stage of International Application No. PCT/US2015/026995, filed on Apr. 22, 2015 which claims priority from U.S. Patent Application Ser. No. 61/984,416 filed on Apr. 25, 2014, and U.S. Patent Application Ser. No. 61/984,466 filed Apr. 25, 2014, all of which are incorporated herein by reference for all purposes.

STATEMENT REGARDING FEDERALLY SPONSORED RESEARCH

This invention was made with government support under cooperative agreement W911NF-14-2-0045 awarded by the Defense Advanced Research Projects Agency (DARPA). The government has certain rights to the invention.

BACKGROUND OF THE INVENTION

This invention relates to systems and methods for cross-diagnostic identification and treatment of neurological features underpinning mental and emotional disorders. More particularly, this invention relates to a multi-modal imaging technique utilized while administering a transdiagnostic assessment battery to a patient to identify one or more brain regions associated with an emotional or mental disorder. The specific brain region may then be targeted for treatment with brain stimulation techniques.

Mental illnesses, for example, post traumatic stress disorder (PTSD), depression, and addiction, impair war fighters and civilians, and are a leading cause of disability and lost productivity. These illnesses can be conceptualized as brain disorders of malfunctioning neural circuits. Often, psychiatric treatments fail to cure a substantial fraction of patients, who are then declared resistant to approved therapeutic interventions. At the core of the problem is the focus on historical diagnostic categories. The National Institute of Mental Health's (NIMH) Research Domain Criteria (RDoC) project aims to develop neuroscience-based classification schemes for diagnosis and treatment of neural circuitry dysfunction. Diagnostic and Statistical Manual (DSM) diagnoses are not neurobiologic entities, but are a historical checklist-based approach of clustering symptoms used to define hypothetical constructs or syndromes. Those syndromes may not align with underlying neurobiological dysfunction in neural circuitry and corresponding behavioral (functional) domains.

Thus, attempts have been made using responsive brain stimulation systems to treat mental and emotional disorders previously treated by psychiatrists. Responsive brain stimulation is stimulation applied to the brain that responds directly to a patient's electrical brain activity or clinical features. One realization of a responsive brain stimulation system is implantable, with electrodes placed inside a patient's brain. There are a number of sites in the brain where stimulation may be applied in attempts to change a patient's emotional experiences. However, these responsive brain stimulation systems often have no proven biomarker. A biomarker may be a measurable indicator or signal from the brain or body representative of the symptoms of the illness being treated that indicates whether the symptoms have gotten better or worse. Without something reliable to sense, it is difficult for the responsive stimulator to respond accurately.

Other attempts to treat mental and emotional disorders have moved away from trying to find biomarkers for specific mental disorders, and instead have tried to find biomarkers for emotions utilizing an affective brain-computer interface (aBCI). An aBCI in combination with a brain scanner or electroencephalography (EEG) system, for example, can look at signals in real-time and determine whether the subject is having a positive-valence (e.g., happy, pleasant, etc.) or a negative-valence (e.g., angry, afraid, unpleasant, etc.) emotion. In more advanced systems, the specific emotion (e.g., anger, fear, disgust, pleasure, etc.) can be classified.

However, an aBCI alone may not be a useful clinical tool, as it cannot determine whether the emotion is a healthy emotion (e.g., anger that was justifiably provoked, fear because the patient is in a dangerous situation, etc.) from an unhealthy emotion (e.g., violent anger in response to a mild insult, fear of an ordinarily safe situation such as driving on a freeway, etc.). Therefore, there it is difficult for a controller to decide whether the emotion should be corrected or altered by stimulating the brain.

Thus, there is a clinical need for responsive neurostimulators, which sense a patient's brain activity and deliver targeted electrical stimulation to suppress unwanted symptoms. This is particularly true in psychiatric illness, where symptoms can fluctuate throughout the day. Affective BCIs, which decode emotional experience from neural activity, are a candidate control signal for responsive stimulators targeting the limbic circuit. Present affective decoders, however, cannot yet distinguish pathologic from healthy emotional extremes. Indiscriminate stimulus delivery would reduce quality of life and may be actively harmful.

The need for affective BCI monitoring and decoding is clearest in deep brain stimulation (DBS). Psychiatric DBS has been used at multiple targets, with preliminary success in treating depression and obsessive-compulsive disorder (OCD), for example. Progress in psychiatric DBS, however, has been limited by its inherent open-loop nature. Present open-loop DBS systems deliver energy continuously at a pre-programmed frequency and amplitude, with parameter adjustments only during infrequent clinician visits. This has led to more rapid depletion of device batteries which requires battery replacement surgeries and introduces the patient to associated pain and/or infection. The continuous delivery of energy also leads to an increased side-effect burden. Side effects in particular derive from present devices' inability to match stimulation to a patient's current affective state, brain activity, and therapeutic need. Atop this, many disorders have symptoms that rapidly flare and remit, on a timescale of minutes to hours. This is particularly common in the anxiety and trauma related clusters. Existing open-loop DBS strategies have been unable to effectively treat such fluctuations, because the fluctuations occur on shorter timescales than the infrequent clinical visits.

However, development of closed-loop emotional DBS systems has been blocked by a lack of accurate or feasible biomarkers. Three major challenges arise when considering existing affective BCIs as the sensing component of closed-loop DBS control. First, many identified neural correlates of affective disorders cannot be continuously monitored in the community. Functional magnetic resonance imaging (fMRI) can provide deep insights into activity across the whole brain, and has been demonstrated for partial affective classification in real time. Similar results have been seen with near-infrared spectroscopy (NIRS), which also measures blood-oxygenation signals. The former, however, requires bulky machines and is not compatible with implanted devices, and the latter has not yet been demonstrated in an online-decoding paradigm. Moreover, although NIRS can be reduced to a wearable/portable device, it requires an externally worn headset. Given the unfortunate persistence of stigma attached to patients with mental disorders, few would wear a visible display of their illness, even if it did control symptoms.

Another challenge with existing affective BCIs is that affective decoding modalities that support continuous recording may not function properly in the presence of psychiatric illness. Electrocorticography (ECOG) is a promising approach, as it can be implanted, and thus hidden, with relatively minimally invasive surgery. ECOG signals offer temporal resolution and may be able to use decoders originally developed for electroencephalography (EEG). Non-invasive EEG has been a successful approach in affective BCI, with some real-time decoding of emotional information. Uncertainty arises because all successful EEG affective decoding has been demonstrated in healthy patients. Patients with mental illness, particularly those with treatment-resistant disorders, by definition do not have normal or healthy neurologic function. Furthermore, recent experiences with EEG in psychiatry suggest that measures that accurately decode healthy controls may not transfer to patients. EEG biomarkers that initially appeared to correlate with psychiatric symptoms and treatment response have often not held up under replication studies. This is at least in part because psychiatric diagnosis focuses on syndromes and symptom clusters, not etiologies. There is a wide consensus that clinical diagnoses generally contain multiple neurologic entities, and that the same clinical phenotype might arise from diametrically opposite changes in the brain. This may present a challenge for clinical translation of existing affective decoders.

Yet another challenge with existing affective BCIs is that even if affective BCIs can function in the presence of clinical symptoms, they may not be able to adequately distinguish pathologic states. Newer affective BCI algorithms may yet be shown to accurately classify emotion even in the presence of abnormal neural circuit activity, but this is only part of the need. Psychiatric disorders are marked by extremes of the same emotions that occur in everyday normal life. The difference is not the degree or type of affect, but its appropriateness to the context. PTSD is one clear example where patients with this disorder over generalize from a fearful event and experience high arousal and vigilance in contexts that are objectively safe. It is likely possible for an affective BCI to detect high arousal in a patient with PTSD in uncontrolled real-world environments. It is less clear whether any algorithm could distinguish pathologic arousal (e.g., a 'flashback' in a grocery store, confrontation with trauma cues, etc.) from healthy variance (e.g., riding a roller coaster, watching an exciting movie, etc.). These emotions would be very difficult to differentiate solely on the basis of experienced affect, and yet the use of brain stimulation to neutralize the latter set of experiences would negatively impact the patient's quality of life.

The above described challenges combine to reveal a final complication. In a fully implanted system, onboard storage and computational resources are limited, and therefore it may not be possible to perform decoding and tracking over long periods of time. Thus, affective decoders are caught in a dilemma of temporal resolution. If the affective decoders are tuned to respond to brief but intense events, the decoders may over-react to natural and healthy emotional variation. If the decoders instead focus only on detecting and compensating for long-term trends, sharp but short exacerbations will go uncorrected, decreasing patients' quality of life and continuing the problems of existing open-loop DBS. In the very long run, these problems may be ameliorated by improvements in battery and processing technology. However, regulatory agencies require extensive review of all new technology components, meaning that a new battery could take a decade to reach clinical use even after being successfully demonstrated for non-implantable applications. Processors might be more easily upgraded, but increased processing power means increased heat, which cannot be readily dissipated inside the body.

Thus, there is a need for systems and methods for responsive decoding and stimulation capable of operating within the limits of current clinical technology. An affective BCI usable as the sensing component of a responsive brain stimulator and capable of inferring emotional state from neural signals to enable a responsive, closed-loop stimulator is desirable. It is also desirable for continuous monitoring capable of indicating that the system is moving into a pathological state so that the controller can adjust parameters of an implanted DBS to counteract that trajectory, as well as reduce the side effects of over-stimulation, alleviate residual symptoms that may relate to under-stimulation, and improve power consumption for a longer battery life.

SUMMARY OF THE INVENTION

The invention overcomes the aforementioned drawback by providing a system and method for treating patients with mental or emotional disorders utilizing an affective BCI component in a closed-loop, symptom-responsive psychiatric DBS system. Plasticity and volition components are incorporated into the affective BCI for control of neurostimulation. The systems and methods may be useful for patients with symptoms in the mood (e.g., depression, bipolar disorder, etc.), anxiety (e.g., generalized anxiety, panic disorder, etc.), obsessive-compulsive (e.g., obsessive-compulsive disorder, Tourette syndrome, etc.), and trauma/stress-related (e.g., post-traumatic stress disorder, etc.) clusters, as well as patients with certain types of brain damage, such as white matter injury.

Regarding plasticity, in some embodiments, a BCI may be built by having participants perform a 'predicate task', such as hand movement, motor imagery, or emotional imagery in the case of affective BCI. The transdiagnostic tasks described below may also be considered as predicate tasks. From neural activity during this training period, a decoder is built, then deployed to classify new brain activity as it arises. As the BCI learns the mapping between brain signals and task variables, the brain changes to better match the decoder. The brain's inherent capacity for plasticity will remap cortical signals to produce improved information for the BCI. It is also possible to create a BCI where there is no predicate task, and where the decoder is simply initialized with arbitrary parameters. This is sometimes referred to as a 'direct control' system, and has been shown to be an effective way of building a BCI that is computationally efficient. The brain still changes and learns to use this type of decoder effectively.

The volition component of affective BCI in closed-loop psychiatric DBS includes a patient sensing that present stimulation parameters are not well matched to his/her clinical needs, then choosing to alter the stimulation parameters by deliberately modulating specific aspects of brain activity (e.g., firing rates of specific neurons, power in certain bands of local field potential (LFP), EEG, ECOG, and the like). The list is not exhaustive; a wide range of standard signal transforms could feasibly and reasonably be applied to the signals and could be under a patient's volitional control. The volitionally controlled component may resolve some of the limitations identified above, such that affective decoding would not need to directly classify an emotion as pathologic vs. healthy-extreme. Rather, the patient can express his/her desire directly and efficiently through a BCI, and the question of whether to optimize response to fast or slow time-scales becomes moot. Thus, stimulation can be adjusted when the patient explicitly requests the affective controller to do so. Heterogeneity of biomarkers within clinical disorders may also be controlled for, because the primary decoded variable is the patient's own intention to receive mood altering neurostimulation. That said, with adequate application of the transdiagnostic methods detailed below, it may be less necessary to control for heterogeneity, because the clinical diagnosis will not be the principal method for selecting an intervention.

In one aspect, the invention provides a method for diagnosing mental or emotional disorders. The method includes administering, using a computer interface, a transdiagnostic assessment to a patient, the transdiagnostic assessment including at least one psycho-physical task. A series of input data related to a brain of the patient is acquired while the patient performs the at least one psycho-physical task. An impairment corresponding to the patient along a set of functional domains is determined. A signal recorder is used to record at least one of electrical, magnetic, optical, bio-acoustic, brain derived or body derived activity from the patient. The method further includes identifying, from the at least one psycho-physical task, a deviation in the set of functional domains as compared to a predetermined set of control subjects. Brain regions and signal characteristics are identified from the input data corresponding to the identified deviation. One or more stimulation devices are used to apply stimulation to the identified brain regions to alter the at least one of electrical, magnetic, bio-acoustic, brain derived or body derived activity in the brain regions and their connected regions.

In another aspect, the invention provides a system for diagnosing mental or emotional disorders. The system includes a computer interface for administering a transdiagnostic assessment to a patient, the transdiagnostic assessment including at least one psycho-physical task. An acquisition device acquires a series of input data related to the brain of the patient while the patient performs the at least one psycho-physical task to determine an impairment corresponding to the patient along a set of functional domains. A signal recorder records the at least one of electrical, magnetic, bio-acoustic, brain derived or body derived activity from the patient. A processor is coupled to the computer interface and configured to identify, from the at least one psycho-physical task, a deviation from the set of functional domains as compared to a predetermined control, and identify brain regions and signal characteristics from the input data corresponding to the identified deviation. At least one stimulation device applies stimulation to the identified brain regions to alter the at least one of electrical, optical, magnetic, bio-acoustic, brain derived or body derived activity in the brain regions. Stimulation may be applied for therapeutic purposes, or to cause effects within the brain that probe its networks as they respond to the task.

These and other features, aspects, and advantages of the present invention will become better understood upon consideration of the following detailed description, drawings and appended claims.

BRIEF DESCRIPTION OF THE DRAWINGS

FIG. 7 is a table of example functional domains for transdiagnostic assessment, corresponding functional tasks for probing each functional domain, and brain regions known to be involved in performance/impairment for each functional domain.

Like reference numerals will be used to refer to like parts from Figure to Figure in the following description of the drawings.

DETAILED DESCRIPTION OF THE INVENTION

Figure 1:
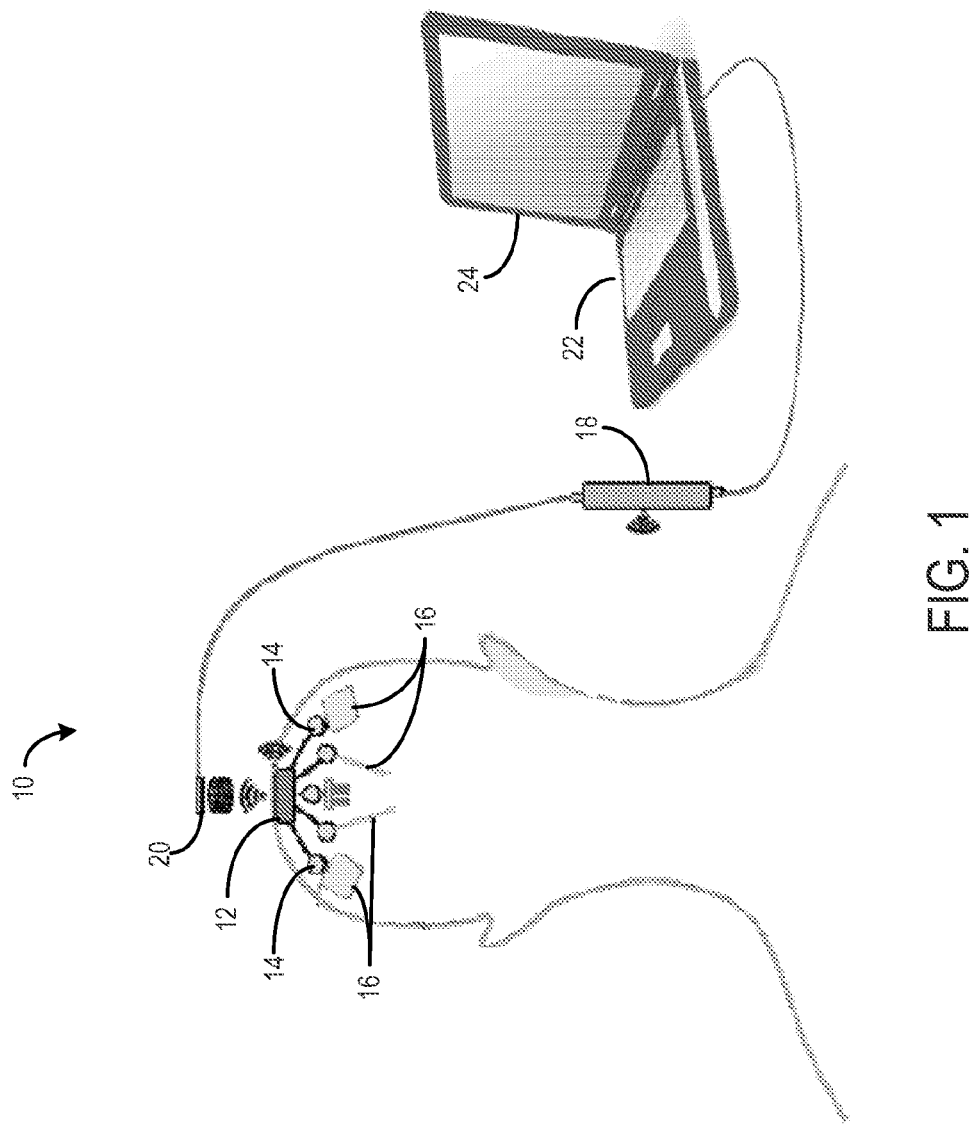
FIG. 1 is a schematic illustration of a system for diagnosing and treating psychiatric patients using a transdiagnostic assessment and activation of one or more brain regions in accordance with the present invention.
Figure 2:
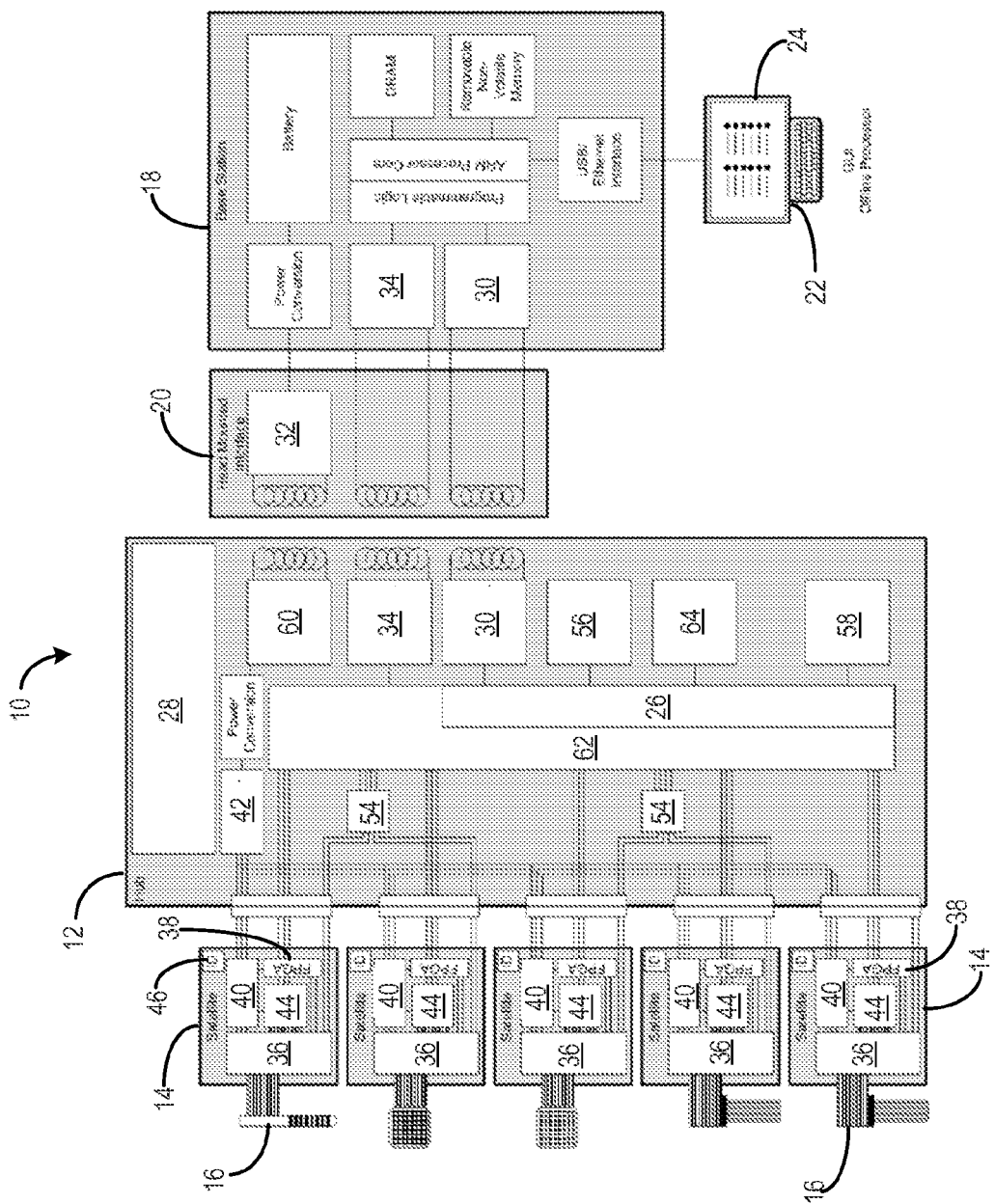
FIG. 2 is a block diagram of the system illustrated in FIG. 1.

FIGS. 1 and 2 show an affective BCI component in a closed-loop, symptom-responsive psychiatric DBS system 10. The system 10 may be capable of diagnosing patients not by clinical, symptom-focused interview, but by transdiagnostic assessment of objective measurement of the patient's performance on quantitative tests of psychological function. The system is configured to link the transdiagnostic symptom assessment to a treatment that specifically activates or de-activates one or more brain areas via DBS. More specifically, the system 10 is designed to record and decode neural information from specific dysfunctional networks associated with specific symptoms, behaviors and then deliver stimulation to these networks to afford symptom relief and measurable improvements in dysfunctional behaviors. The patient may be given control over the stimulation system's actions through a hybrid BCI algorithm that monitors the patient's intentions. Closed-loop algorithms further focus the treatment not only in space (i.e., region of the brain) but in time, so that stimulation occurs only when the patient needs it.

The system 10 generally includes a central decoding and controlling hub 12, connected satellite modules 14 that deliver stimulation and recording through electrodes 16, for example, existing commercial electrodes and innovative electrodes offering high channel counts with integrated low-power signal conditioning. In some embodiments, the hub 12 and satellite modules 14 may be a single implanted module. Either part may also exist outside the body and communicate wirelessly to the electrodes 16. The hub 12, or implanted module, may be implanted under the scalp of a patient and can wirelessly communicate with an external base station 18 for data streaming, reprogramming, wireless recharge, and coordinating intervention across sites to enhance treatment of neuropsychiatric dysfunction. Alternatively, the hub 12 may itself be wearable or otherwise non-implanted, or the hub 12 and base station 18 may be merged as a single component. The base station 18 is in electrical communication with the hub 12 via a head mounted interface 20 and, in some embodiments, may interface with an offline processor 22 having a user interface 24, such as a clinician interface. The head mounted interface 20 may be a wearable processing unit that communicates, configures, and can control the implanted system 10. The head mounted interface 20 might also mount or implant to some other body part (e.g., chest) depending on the surgical clinician's preference. In some embodiments, a hand held patient controller (e.g., a watch) may be provided for self-reporting and triggering recordings, as well as monitoring heart rate wirelessly, skin conductance, and the like.

The implantable system 10 may be designed to record and stimulate brain circuits. The configuration shown in FIGS. 1 and 2 is an example of bilateral electrode satellite placement. In one non-limiting example, some of the electrodes 16 may be recording electrodes that consist of cortical ECoG arrays recording from the dorsolateral prefrontal cortex (dlPFC) and subcortical DBS leads recording from the ventromedial prefrontal cortex (vmPFC). Stimulation may be performed with subcortical DBS leads placed in the nucleus accumbens (NAcc) and ventral capsule/ventral striatum, for example. One of more of the electrodes 16 may be a recording or stimulating electrode in this configuration. Additionally, or alternatively, any of the electrodes 16 may be replaced with one of several commercial designs capable of recording single units.

Algorithms stored on the hub 12 may enable the system 10 to merge spike and field-potential data to estimate the patient's psychiatric state and deliver therapeutic stimulation. The frequency of stimulation delivery may depend upon how frequently neural signatures that trigger stimulation occur. Those signatures may be fully or partly under a patient's direct intentional control. Real-time telemetry may enable a clinician, for example, to tune algorithm parameters as required by the patient. Thus, the system 10 will also provide neuroscientists an unprecedented view of real-time brain activity in fully conscious patients interacting with real-world environments.

The system 10 may be configured to operate in one or more modes. For example, in autonomous mode, the hub 12 may be controlled by an internal processor 26 and powered by an internal battery 28 that can be recharged periodically, as shown in FIG. 2. Low-bandwidth (e.g., 2 MBps) telemetry 30 may be used to report on the hub's state of health and provide the subject comfort in the ability to both wake up and put the system 10 to sleep when needed. In a continuous recharge mode, the head-mounted interface 20 can be attached to the base station 18 to wirelessly power the implanted device via a charger 32. The continuous recharge mode may be desirable when operating the system 10 in modes that consume more power. In a base station control mode, a high-bandwidth telemetry link 34 can be used to stream live neural data to be processed within the base station 18, which can then control stimulation therapies over the low-bandwidth telemetry 30. The base station control mode permits higher-power algorithms to be implemented without burden on the hub 12 and satellite modules 14. In a computer control mode, the offline processor 22 can be connected through the base station 18 to further increase processing power and provide additional interfaces and resources to researchers and clinicians. The computer control mode may be used during the initial configuration period, where the implanted device may be running suboptimally with high-channel counts and high processing power. As the device and algorithms are iteratively matched to the patients needs, operation may become less dependent upon external modes and move toward autonomous control.

With continued reference to FIG. 2, each satellite module 14 may interface with or be fully integrated into an electrode 16. In one example, the electrodes 16 may be multi-channel macro-electrodes or micro-electrodes. A cross-point switch (CPS) matrix (Neural CPS) 36 may be used to re-configure the electrodes 16 for recording and stimulation. Additionally, the neural CPS 36 may enable multiple electrodes 16 to be simultaneously connected to one of two analog stimulus inputs to create lower impedance larger-area electrode clusters for stimulation. Neural amplification and digitization within the satellite module 14 may provide a higher level of signal to noise ratio (SNR) and reduce the wire-count burden to communicate with the hub 12 through multiplexed data. A field-programmable gate array (FPGA) 38 may reduce wire-counts and provide control over the Neural CPS 36 and amplifier. The FPGA 38 may also provide charge-balanced communication with the hub 12, which mitigates risks of tissue damage caused by DC leakage currents. Power may be provided by an AC power supply 40 that will convert an AC supply 42 provided by the hub 12 into DC voltages required by the satellite modules 16.

As previously described, the system 10 may be capable of recording several types of neural signals (e.g., Spikes, LFPs, ECoG, etc.) from different types of electrodes 16 (e.g., Micro-, DBS, ECoG arrays, etc.). This requires the satellite 14 to include a neural amplifier 44, such as a multi-purpose re-configurable neural amplifier that is both low-noise and low-power. Low noise may be necessary to capture small LFP and ECoG features in high gamma frequency bands, while low power may be necessary to reduce heat dissipation and extend the operational lifetime.

Each satellite module 14 may include a unique ID 46 that is linked to its specifications, internal components, manufacturing data, and attached electrodes 16. The satellite's 14 unique ID 46 may allow the hub 12 to interrogate the connected satellite modules 14 and configure itself based upon returned information. This information may then be transmitted to the base station 18 to be verified and logged. The satellite module 14 may also be configured to monitor and report a set of health parameters that includes electrode impedance and may also include temperature, humidity, supply voltage, and hub-to-satellite lead line integrity, for example. In the case of malfunction, actions may be taken by the hub 12 to modify or shut-down satellite functions.

Figure 3:
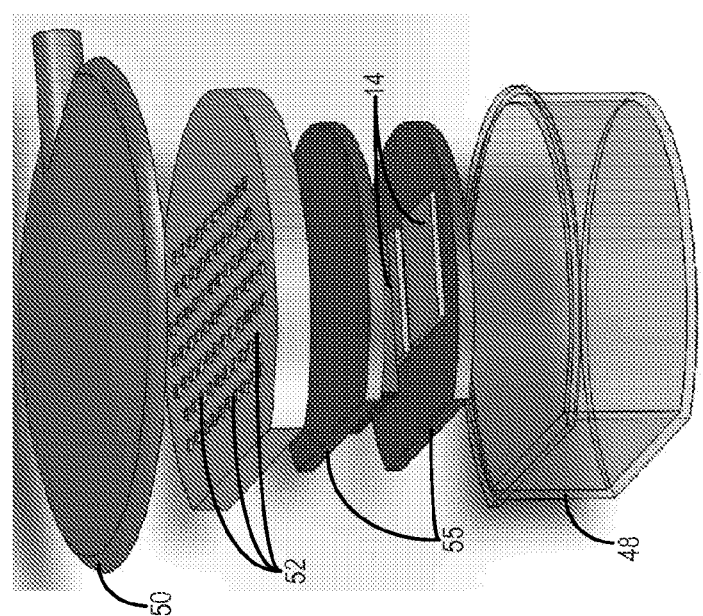
FIG. 3 is an exploded view of a satellite module incorporated into the system of FIG. 2 for delivering stimulation to brain regions.

Turning now to FIG. 3, an exploded view of one of the satellite modules 14 of FIG. 2 is shown. The components of the satellite module 14 may be enclosed within a hermetically sealed housing 48 that is hard-wired to the electrodes 16 and a lead body with a distal connector for inter-operative attachment to the hub 12 (see FIG. 2). The housing 48 may be a titanium package measuring about 14 mm in diameter and about 7 mm in thickness. This package size is targeted so that the satellite module 14 can fit within a standard neurosurgical craniectomy window. A lid 50 made from a ceramic material, for example, may include a plurality of hermetic apertures 52 and may be coupled to the housing 48 to form a hermetic seal. Electronics of the satellite modules 14 may be positioned on two rigid flex boards 55 in stacked configuration. In some embodiments, wires to the electrode arrays 16 and lead cables to the hub 12 may be permanently attached to the satellite module 14.

Returning to FIG. 2, the hub 12 may configure the satellite modules 14, process neural data, decode neuropsychiatric states, control closed-loop neurostimulation therapies, and transmit data to the external base station 18. The hub 12 may include the processor 26, which may be a low-power processing core configured to execute algorithms. The hub 12 may further include one or more current pulse generators 54 for applying stimulation therapies through the electrodes 16. In addition, the hub 12 may include a memory 56, such as dynamic random-access memory, accessible by the processor 26 for stored data. The hub 12 may also include the high-bandwidth telemetry link 34 for neural data exfiltration, and the battery 28, which may be wirelessly charged, for extended operational life.

The current pulse generators 54 for neural stimulation may be positioned in the hub 12 and may be responsible for generating the programmable current-controlled stimulation pulses for neuromodulation. Analog stimulation waveforms may be sent to the satellite modules 14 and routed to stimulation electrodes 16 via the neural CPS 36. In order to effectively modulate stimulation therapies based upon closed-loop neural activity, stimulus waveforms may be dynamically re-programmable by hub algorithms. Waveforms may be biphasic and charge balanced, and voltages across the electrode-tissue interface may be limited to the water window to inhibit chronic tissue damage. For monopolar stimulation, currents may be returned to the conductive hub 12, and for bipolar stimulation, currents may return through adjacent electrodes 16.

With continued reference to FIG. 2, the hub 12 may further include one or more sensors 58 including, for example, humidity, temperature, and accelerometer sensors. Humidity and temperature sensors may be a useful part of health monitoring in the hub 12. For example, an increase in moisture may be detected by the sensor 58 and a warning of failure due to ingress of moisture from the body, or possible accumulation of moisture from parts may be provided. In another non-limiting example, accelerometer data gathered from one of the sensors 58 may be useful for determining subject activity, including sleep, which may be used as a signal for closed-loop control. Measurements acquired from the sensors 58 may be logged and reported to the base station 18. Similar to the satellite modules 14, the hub 12 may include a unique ID, for example a 16 bit unique identifier, that can be read through the low-bandwidth telemetry 30.

As previously described, the hub 12 may include the processor 26 and a control unit 62, such as a programmable logic controller (PLC) to manage system-level functions and execute closed-loop algorithms for adaptive neuromodulation therapy. The processor 26 and control unit 62 may be adaptable and re-programmable in order for closed-loop algorithms to be developed, tested, and tuned for enhanced therapeutic benefit to each patient. The processor 26 and control unit 62 may be capable of configuring satellite modules 14 and receiving neural data, extracting signal features from raw neural data, decoding neuropsychiatric states, modulating stimulation therapy, monitoring and logging system health data, detecting and recording neural data, and managing wireless communication to the base station 18.

The hub 12 may further include a nonvolatile storage module 64. A non-limiting example would be a single-level cell (SLC) flash. SLC flash may have favorable power characteristics and sufficient bandwidth for high channel count raw spike recording. Peak power consumption is below 30 milliwatts, with spike scenarios expected around 17 milliwatts. As requisite data rate decreases (fewer channels recorded or LFPs vs. spikes or features vs. raw), power consumption decreases. Recording 320 channels of LFP (Fs=2000 Hz) is expected to take less than 2 milliwatts. These numbers assume a pre-erased device and page-size writes.

Collection of data may be necessary to understanding brain function in relation to neuropsychiatric diseases and in assessing the effectiveness of the device in treating symptoms. In addition to being able to stream data via the high-bandwidth telemetry link 34, data may be stored internally and later uploaded to the base station 18. Depending upon the type of data desired, varying lengths of recordings may be saved. For example, storing only spike times requires less memory than storing raw spike data.

Figure 4A:
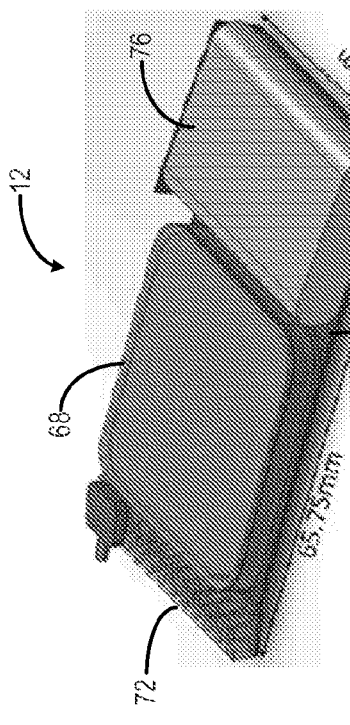
FIG. 4A is a schematic illustration of a controller hub incorporated into the system of FIG. 2 to be implanted under the scalp of a patient for estimating the patient's psychiatric state and delivering therapeutic stimulation.
Figure 4C:
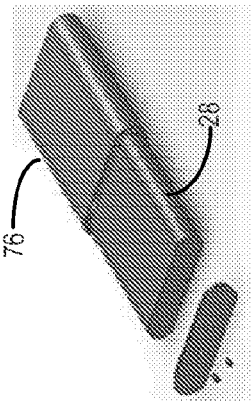
FIG. 4C is an exploded view of a battery and battery package for powering the controller hub of FIG. 4A.
Figure 4B:
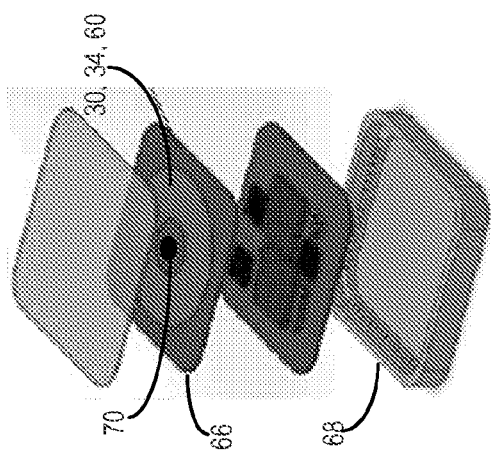
FIG. 4B is an exploded view of a housing for the controller hub of FIG. 4A.

The hub 12 may further include a wireless power link 60 for inductive recharge. Thus, the hub 12 may include three antennas for inductive recharge (wireless power link 60), high-bandwidth telemetry 34, and low-bandwidth telemetry 30. As shown in FIGS. 4A and 4B the antennas 30, 34, 60 may be constructed from PCB micro strip traces, for example, and positioned on an antenna board 66 near the top of a housing 68 where the antennas can be in close proximity to the scalp. A magnet 70 may be positioned in the center of the antenna board 66 to help with alignment with the head mounted interface 20.

A connector 72, such as a high-density connector that may include 64 or more sockets, may be utilized for connection to the satellite modules 14 and may also be connected to the hub housing 68. The connector 72, the battery 28 and the hub housing 68 may be attached by a thin film flex cable 74 and over-molded with medical-grade silicone (not shown), for example. The thinness of the hub 12 components may be desirable for comfortable and unobtrusive implantation on top of the skull, and the flexibility of the hub 12 components may provide a better fit to varying skull curvature. As shown in FIG. 4C, the battery 28 may be contained in a package 76, such as a hermetically-sealed titanium package, and may power the hub 12 components via a multi-layer flex cable, for example. The housing 68 of the hub 12 components may be constructed of low temperature co-fired ceramic (LTCC) which may allow improved performance of the wireless power link 60, high-bandwidth telemetry 34, and low-bandwidth telemetry 30.

Returning to FIG. 2, the base station 18 is coupled to the processor 22 and user interface 24. The user interface 24 may be a display including, for example, LEDs and buttons for basic functions, such as putting the system 10 to sleep, waking the system 10 up, performing a check status, and the like. The base station 18 may also be coupled to the head mounted interface 20 that includes antennas for the high-bandwidth telemetry 34 and the wireless power charger 32. Without the head mounted interface 20 attached, the base station 18 may communicate and control the implanted unit via the low-bandwidth telemetry 34. When the head mounted interface 20 is attached, the high-bandwidth telemetry 34 link may be used to stream real-time neural data to the base station 18 where closed-loop algorithms can be executed at higher power than can be used inside the implant. Closed-loop control may then be achieved by controlling the system 10 over the low-bandwidth telemetry 34 link. This closed-loop control may include a component of directly detecting/decoding the patient's intentions regarding neurostimulation. The head mounted interface 20 may also be used to wirelessly recharge or continuously power the implant via the charger 32.

Figure 5:
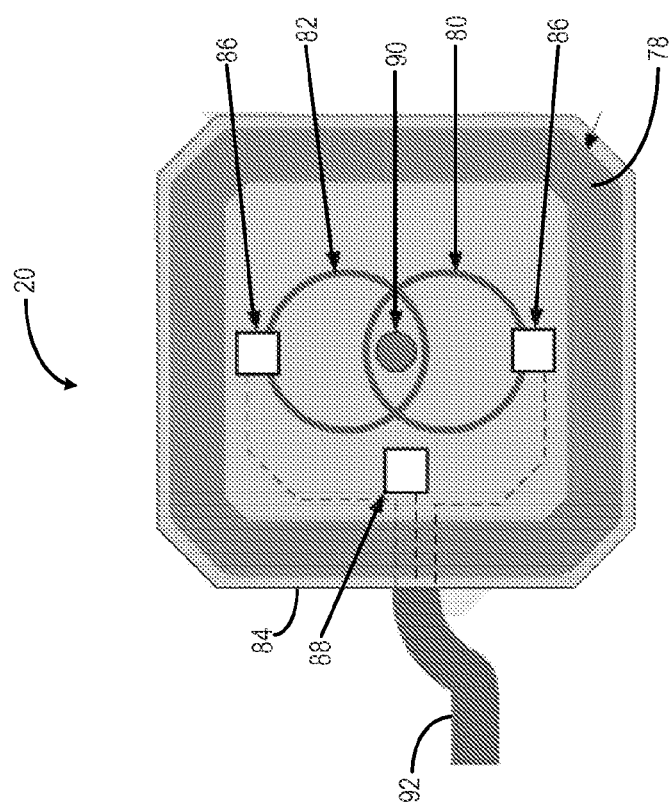
FIG. 5 is a schematic illustration of a head mounted interface incorporated into the system of FIG. 2.

As shown in FIG. 5, the head mounted interface 20 may include a first antenna 78 for the wireless power charger 32, a second antenna 80, such as a transmit antenna, for the high-bandwidth telemetry 34, and a third antenna 82, such as an receive antenna, for the high-bandwidth telemetry 34. The antennas 78, 80, 82 may be mounted on a PCB 84 which also includes matching networks 86, a wireless power amplifier 88, and an alignment magnet 90. The alignment magnet 90 may help to align and retain the head mounted interface 20 with the magnet 70 of the hub 12 to ensure power transfer efficiency and communication. The head mounted interface 20 may further include a cable bundle 92 for connection to the base station 18 that may be soldered directly to the PCB 84, for example. In one non-limiting example, the cable bundle 92 may be a 1 m highly flexible cable bundle including two RF coax cables, as well as DC power and clock signals for the wireless power transmitter. A plastic enclosure (not shown) may protect the PCB 84 from contact by the user. The head module may connect to the base station via a like 1 m highly flexible cable bundle.

In some embodiments, the system 10 may be a non-invasive system for stimulating the brain. That non-invasive realization may collapse components such as the satellites 14, base station 18, and hub 12 into a single part. The non-invasive system may enable not only treatment via induction of brain plasticity, but also pre surgical planning of DBS targets. The non-invasive system may be combined with EEG, for example, to produce a closed-loop system. The non-invasive system may include a plurality of scalp or non-contact electrodes and/or neuro-stimulation coils in communication with a software-controlled helmet, cap, or set of electrodes that can stimulate areas of the brain. The embedded software may steer the amount and polarity of energy sent to each electrode, thus shaping the E-fields and allowing accurate targeting of specific cortical areas. In other embodiments, the non-invasive system may be combined with non-electrical modalities, such as magnetic or ultrasonic stimulation, for stimulating the brain.

Figure 6:
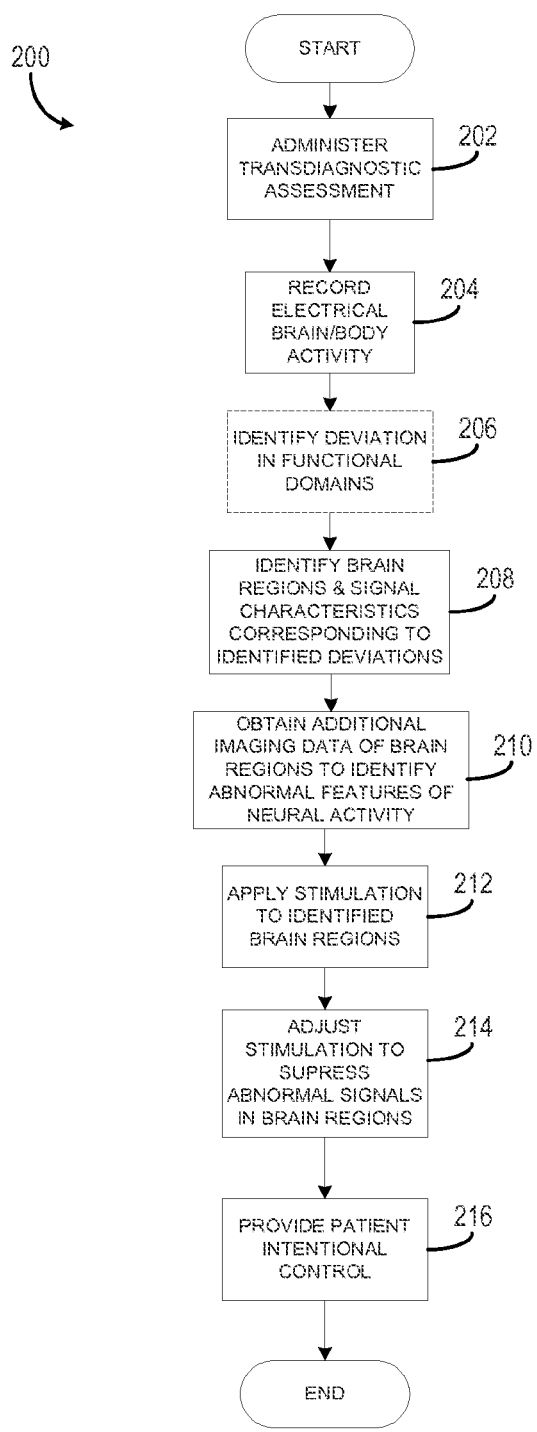
FIG. 6 is a flow chart setting forth the steps of a method for diagnosing and treating mental and emotional disorders by analyzing an individuals brain with both imaging and behavioral testing in accordance with the present invention.

Referring now to FIG. 6, a flow chart sets forth exemplary steps 200 for diagnosing and treating mental and emotional disorders by analyzing an individuals brain with both imaging and behavioral testing. The method incorporates the affective BCI component in the closed loop, symptom—responsive psychiatric DBS system 10 previously described. In general, the method may include performing a series of brain scans on a patient while the patient performs a battery of behavioral tasks. From the patient's performance on the task battery and/or the brain's activations during performance of the tasks, the system 10 may identify what is abnormal for that individual patient in terms of functional domains (e.g., fear, reward motivation, emotion regulation, decision making/impulsivity, attention/perseveration, cognition, etc.) as shown in the table of FIG. 7. The system 10 then may link the patient-specific behavioral measurement to patterns of activation and de-activation across different brain regions, identifying specific structures that are the source of the patient's individual impairment. The system 10 may then use a range of invasive or non-invasive brain stimulation technologies to specifically target the brain regions and provide individualized psychiatric treatment, or to probe the network further to better classify the impairment.

Thus, the method to be described shifts away from treating patients based on conventional classifications of mental diseases and disorders (e.g., The International Classification of Diseases (ICD) or the Diagnostic and Statistical Manual of Mental Disorders (DSM)). Diagnosis-based treatment is the standard of care in psychiatry. However, there is a widespread recognition that the diagnoses do not correlate well to underlying brain circuit dysfunction. For example, a single disorder called "major depression" could be one or more different kinds of brain dysfunction. The NIH has proposed a domain oriented solution, the Research Domain Criteria (RDoC). However, RDoC is meant as a scientific research tool, not a clinical system or diagnostic tool. Thus, the present system and method enable a shift to functional-domain diagnosis using behavioral testing that consider more abnormal domains as the "problem" to be treated.

Returning to FIG. 6, the method may begin by administering a transdiagnostic assessment at process block 202. Administering the transdiagnostic assessment requires a patient to perform one or more psycho-physical tasks to determine the patient's impairment along a set of functional domains. The functional domains, as shown in the table of FIG. 7, may be validated psychological constructs that are transdiagnostic and occur in multiple named mental disorders (e.g., PSTD, MDD, generalized anxiety disorder (GAD), traumatic brain injury (TBI), substance use disorder (SUD), borderline personality disorder (BPD), pain disorder, etc.). The disorders shown in bold represent the primary domains for the disorder.

The functional domains are not limited to those shown in FIG. 7, and in one non-limiting example, the system 10 may be configured to access the NIMH's RDoC Matrix for additional functional domains. Each functional domain may be measured by one or more corresponding behavioral tasks that probe each domain and certain brain regions known to be involved in performance/impairment for each domain. The various brain regions may include, but are not limited to the rostral anterior cingulate (rACC), dorsolateral prefrontal cortex (dlPFC), ventromedial prefrontal cortex (vmPFC), orbitofrontal cortex (OFC), subgenual anterior cingulate (cg25), amygdala, anterior insula, thalamus, periaqueductal gray, ventral striatum, subthalamic nucleus, hippocampus, dorsal striatum, and the like.

The transdiagnostic assessment, optionally administered at process block 202 of FIG. 6, may be performed by the patient on a computer, for example, and may be one or more simple computer games that are each designed to probe functioning in a different domain. As a non-limiting example, the tasks outlined below will be described with respect to a patient who has a difficulty with fear regulation (a subset of difficulties with emotion regulation) which may commonly be found in a patient who has PTSD, but can also be seen in obsessive-compulsive disorder, generalized anxiety disorder, panic disorder, and sometimes major depressive disorder. Such a patient may have several psychiatric diagnoses, for example, a prototypical patient may be a returning service member who had been diagnosed with PTSD, but also with an alcohol use disorder and subthreshold depressive symptoms. All of the below descriptions of task-based diagnostics and resulting stimulation protocols may be combined with the patient-intention controller described in below to form a hybrid brain-computer interface.

Figure 8A:
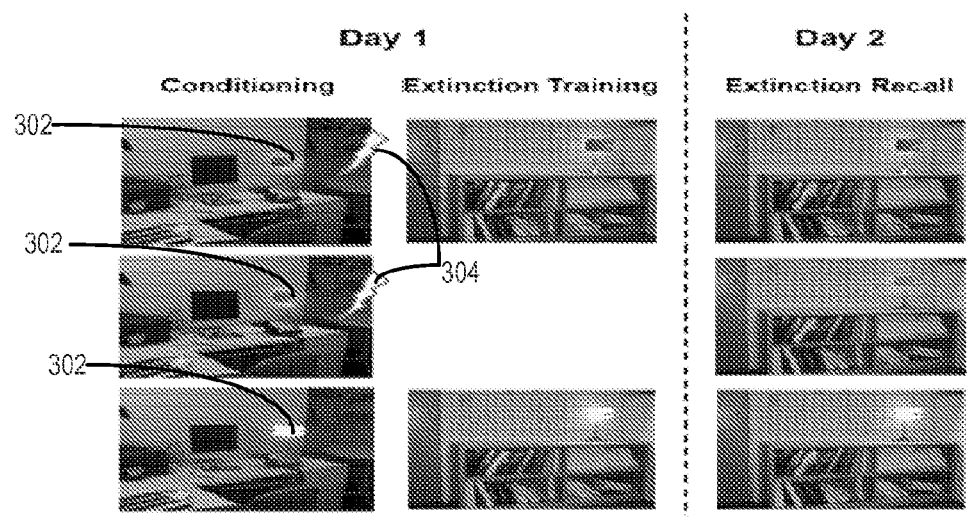
FIG. 8A is an image of an example transdiagnostic assessment task for measuring the functional domain of fear extinction.

Turning to FIG. 8A, a fear learning and extinction task is shown for measuring the functional domain of fear extinction. Performance on this task assesses integrity of the fear and fear suppression systems. The fear learning and extinction task may be impaired for the example PTSD patient described above. During fear conditioning, the patient may be presented with a conditioned stimulus 302, such as multiple, different colored lights. Two of the lights, for example, may be paired with the presence of an unpleasant, but not painful electrical current applied to the fingers of the subject, which is called an unconditioned stimulus 304. This pairing induces conditioned fear responses, such as increased heart rate (HR) and skin conductance response to the presentation of the conditioned stimulus 302. In some embodiments, the fear responses may be measured through biomarkers. The conditioning phase happens outside the imaging scanner before an initial scan.

During an extinction phase, which happens in the imaging scanner, the patient may be presented with the conditioned stimulus 302 in the absence of one or more of the unconditioned stimuli 304 (i.e., one of the lights is "extinguished"—repeatedly re-presented without the shock, so the patient learns it is now safe.), which leads to abolishment of the conditioned responses. The degree of extinction recall (i.e., how much the extinction has been consolidated) is then assessed by a repetition of the extinction trials in the scanner on a second scanning day. For example, during the recall phase, the patient may be presented with both the feared and safe lights. Patients with deficits in fear extinction learning either are unable to learn that one of the lights is safe on Day 1, or will learn this but not recall it on Day 2. A patient with difficulty learning safety may show elevated fear biomarkers (e.g., heart rate, heart rate variability, eye pupil diameter, skin conductance due to sweating, etc.) compared to normal controls at multiple phases of the task.

Figure 8B:
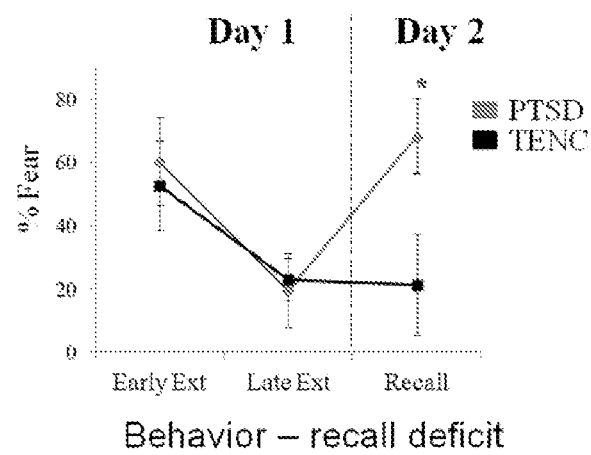
FIG. 8B is a graph illustrating a percentage of fear over various phases of the transdiagnostic assessment task of FIG. 8A for a PTSD patient and a population average.

As shown in the graph of FIG. 8B, the PTSD subject shows impaired recall on Day 2 compared to a population norm. In other disorders, such as MDD, a patient may exhibit extinction deficits (threat bias). Similar to PTSD patients, patients with GAD may show impaired recall, while TBI patients may exhibit impaired extinction learning. SUD patients may exhibit impaired fear acquisition (reward bias), and BPD patients may exhibit rapid acquisition, impaired extinction, and maybe impaired recall, while pain patients may exhibit impaired extinction and recall.

Figure 9:
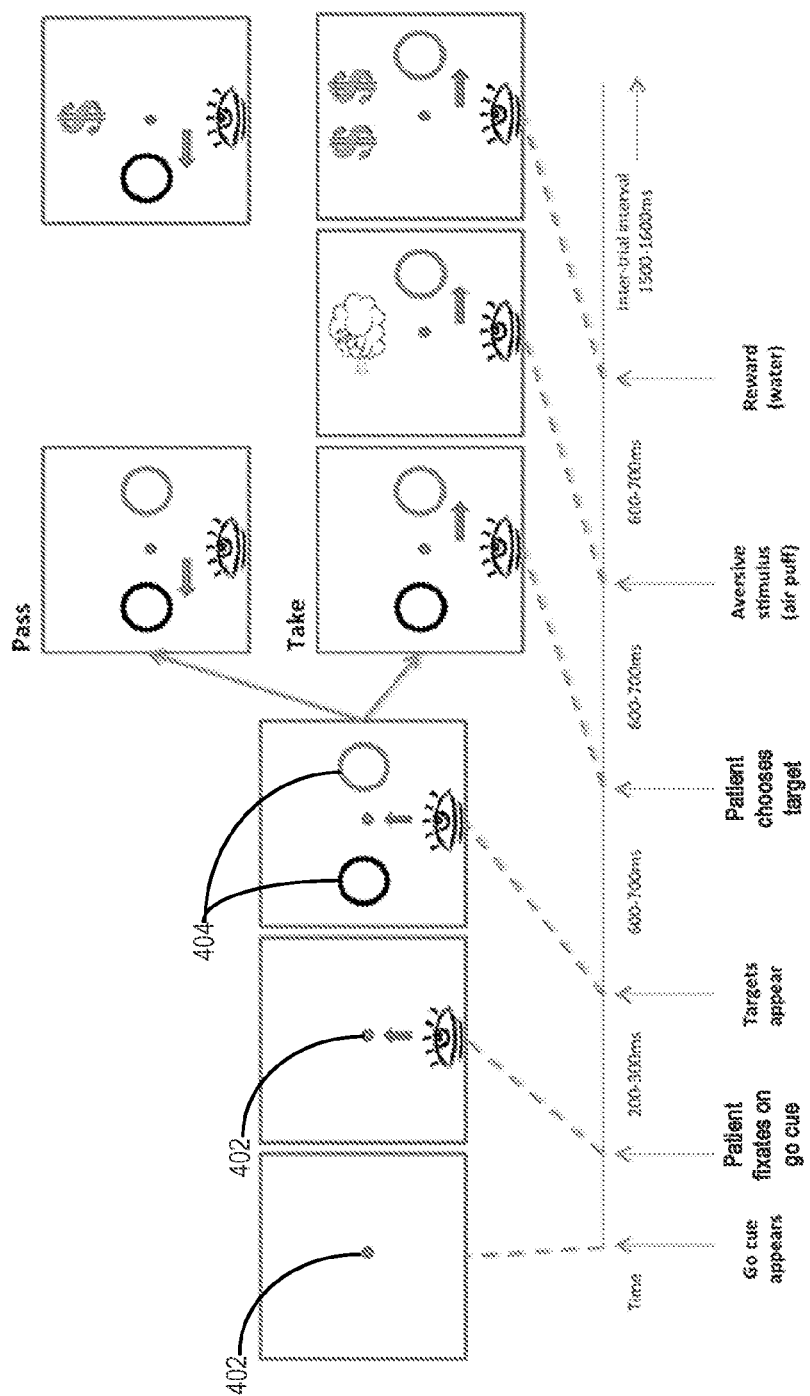
FIG. 9 is schematic illustration of an example transdiagnostic assessment task for measuring the functional domain of reward motivation.

Turning to FIG. 9, an example aversion reward conflict (ARC) task is shown for measuring the functional domain of reward motivation. Performance on this task assesses whether the patient will accept a certain amount of punishment to obtain a certain amount of reward, as well as the patient's reaction time. The ARC task may be impaired for the example PTSD patient described above.

During the ARC task, the patient may be trained on a simple two-choice discrimination task. The patient's performance on each trial may be modified by the expectation of both rewards (e.g., monetary rewards) and aversive stimuli. In the ARC paradigm, the task begins with the patient fixating on a central point 402 on a computer monitor, a shown in FIG. 9. Next, two cues 404 represented as circles are presented on the periphery of the computer monitor. One cue is the combined option cue that represents two distinct stimuli: the probability of aversion and an expected reward of varying magnitude. The probability of aversion is indicated by a color of the cue (e.g., Blue: low, 10%; Black: medium, 50%; Red: high, 90%) and consists of a half second shock to the fingertips. Additionally, or alternatively, the unpleasant punishment may be an air puff to eye or a loud noise, for example. For reward, the magnitude is determined by a thickness of the cue (e.g., Thin: small; Medium: medium; Thick: large). In some embodiments, the reward is represented by pictures of money (e.g., small ($0.10), medium ($0.25), and large ($1.00)). The other cue may be a white "pass" circle that predicts a smaller reward ($0.01) as a safe alternative with no aversion. The subjects must choose either the left hand or right hand cue 404 by pressing the corresponding button on a button box, for example. The side of the screen in which the cues 404 are presented in each trial may be randomized.

Thus, the ARC task can measure how often a patient takes the risk choice overall, for example. In addition, the ARC task can measure what level of reward, and what level of risk-reward balance, is needed to get the patient to run the risk of punishment, as well as the patient's reaction (i.e., how long does the patient take to choose). The ARC task can further determine how the patient's choice may change immediately after the patient "bet wrong" and received punishment.

In one example, the system 10 may incorporate DBS to modify ARC behavior. For example, the NAcc brain region may be stimulated to increase reward sensitivity, the STN brain region may be stimulated to decrease impulsivity, and the Amygdala brain region may be stimulated to increase or decrease threat sensitivity.

The ARC task may show that the example PTSD patient is more driven by threat than reward. In other disorders, such as MDD, the ARC task may show decreased reward sensitivity, possibly with increased threat sensitivity (dissociable). Similar to PTSD, the ARC task may show that a GAD patient and/or a BPD patient is more driven by treat than reward. TBI patients may show faster response speeds and insensitivity to punishment from the ARC task. A SUD patient may be more driven by reward than threat, and a pain patient may be more driven by threat than reward and show an overall lower aversion threshold.

Figure 10:
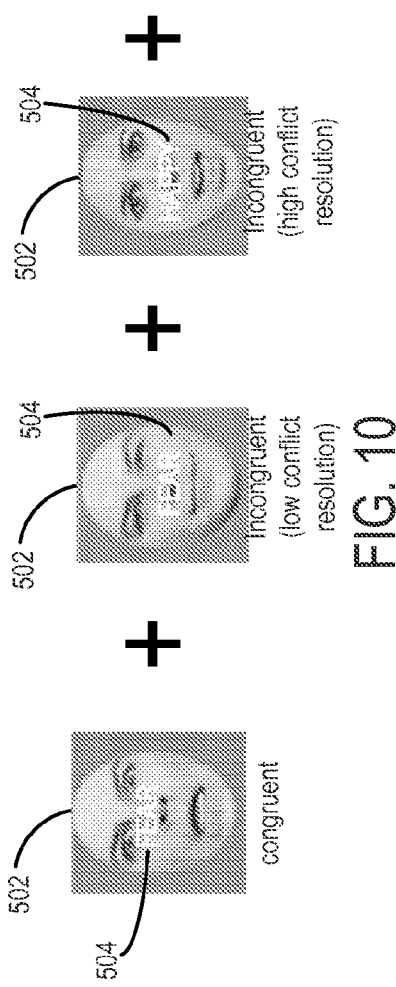
FIG. 10 is schematic illustration of an example transdiagnostic assessment task for measuring the functional domain of emotion regulation.

Turning now to FIG. 10, an emotion conflict resolution (ECR) task is shown for measuring the functional domain of emotion regulation. Performance on this task assesses a patient's reaction time, as a measure of conflict. The ECR task may be impaired for the example PSTD patient described above. During the ECR task, the patient may be shown one or more images 502 of a person showing an emotion. A word 504 describing an emotion is displayed over the image 502. The patient is asked to report the emotion shown in the image 502 while attempting to ignore the word 504 by pressing a 1 (fearful) or 2 (happy) key on a button box, for example. Trials are either congruent (facial expression and word match; e.g., happy expression and the word "HAPPY"), or incongruent (facial expression and word do not match, e.g. happy expression and the word "FEAR"). The task is designed to measure the ability to regulate emotions and adapt behavior after being presented with the initial "surprise" of incongruent stimuli. The presentation of an incongruent image after seeing a congruent image encodes the initial recognition of emotion conflict ("low conflict resolution"). The presentation of an incongruent image followed by a second incongruent image encodes the ability to regulate the emotion conflict and continue performing the task, or behavioral adaptation ("high conflict resolution").

Thus, the ECR task can generate affective responses, while also evoking top-down processing and stressing that network. In addition, the ECR task can identify both cognitive conflict and the response of the brain to highly salient affective stimuli to understand the interaction (i.e., how does a patient become differentially biased to process emotions when under load?) and the dissociation (i.e., how does X get processed when Y is controlled for?). The ECR task can also measure how slowed down a patient is by conflicting emotions, or by fearful instead of happy faces shown in the images 502, for example. The ECR task may also identify whether seeing an image 502 with a fearful emotion makes the patient more error-prone.

The ECR task may show that the example PTSD patient, GAD patient and/or BPD adapts more slowly to conflict when emotion distracts. The ECR task may show that a MDD patient has faster response time on negative-affect stimuli and more difficulty with incongruent images 502 and words 504. TBI and SUD patients may show primarily incongruence without affective component (except from comorbidities). A pain patient may show similar results as a GAD patient. In one non-limiting example, the ECR task may show abnormal behavior in a patient with depression when compared to controls. That patient would be expected to also endorse greater difficulty with regulation emotions using a standardized clinical rating scale.

Further, the patient with depression, for example, may exhibit greater recruitment relative to the healthy controls of brain structures identified as key regions for processing negative affect and salience; specifically, the amygdala, insula, and rostral anterior cingulate (rACC). By contrast, the healthy controls may show greater recruitment of structures identified as key regions for the regulation of emotion and attentional control; specifically, the dorsal anterior cingulate (dACC) and the dorsolateral prefrontal cortex (DLPFC).

Patterns of functional connectivity between brain regions showing differential activation in the patient with depression and healthy controls and other key regions subserving emotion processing and cognitive control of emotion may be analyzed. This analysis may further identify where and how the individual patient is deviating from healthy individuals along distributed neural networks subserving these processes.

Healthy controls may demonstrate strong cohesion in activation between the amygdala and cognitive control regions (DLPFC, dACC, rACC). By contrast, the patient with depression and ADHD may demonstrate low cohesion between the amygdala and cognitive control regions. In particular, lower amygdala-rACC functional connectivity may be found relative to healthy controls. Additionally, healthy controls may demonstrate strong functional connectivity between the amygdala and dACC during High Conflict Resolution (emotion regulation) relative to Low Conflict Resolution (emotion conflict recognition). In contrast, the patient with depression and ADHD may show a reduction in cohesion between amygdala and dACC during High Conflict Resolution. Thus, specific altered connectivity in a known network of emotion regulation, one that is linked both to the specific task and to the general diagnosis (depression) can be identified in the individual patient.

The above described analyses may reveal strong correlations between the strength of functional connectivity between the rACC and dACC and 1) reaction time (behavior); 2) emotion regulation measures (psychological functioning); and 3) psychiatric symptoms and impairment. Those signatures may differ substantially between individual patients. Therefore, a specific brain signature, at the slow metabolic time course detectable with fMRI, that has clinical implications may be identified.

In one example, the system 10 may incorporate DBS to modify ECR behavior. For example, the dACC, VC/VS and dlPFC brain regions may be stimulated to increase the patient's ability to process conflict. Additionally, or alternatively, the Amygdala brain region may be stimulated to lower threat bias and affective activation to reduce distractions.

Figure 11A:
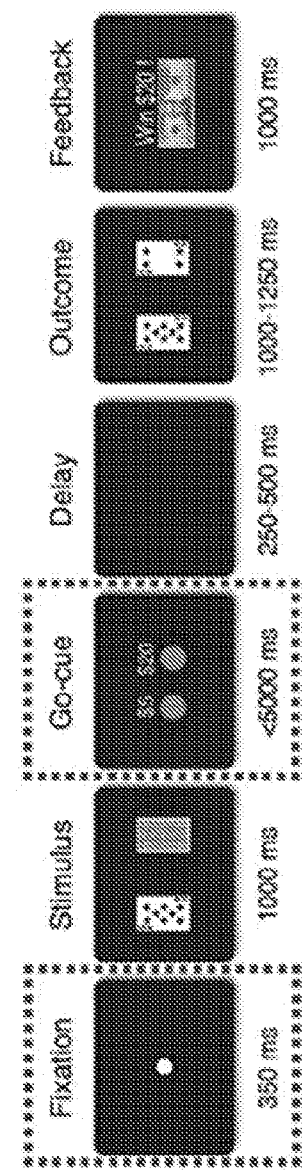
FIG. 11A is a schematic illustration of an example transdiagnostic assessment task for measuring the functional domain of decision making and impulsivity.

Turning now to FIG. 11, a gambling task is shown for measuring the functional domain of impulsivity and decision making. Performance on this task assesses an overall percentage of time the patient bets their card, as well as reaction times and responses to losses. For example, a "rational" person will typically bet their card around 50% overall and show specific patterns on specific cards. If the patient bets more or less than 50% overall the system may identify risk/reward problems with the patient.

Figure 11C:
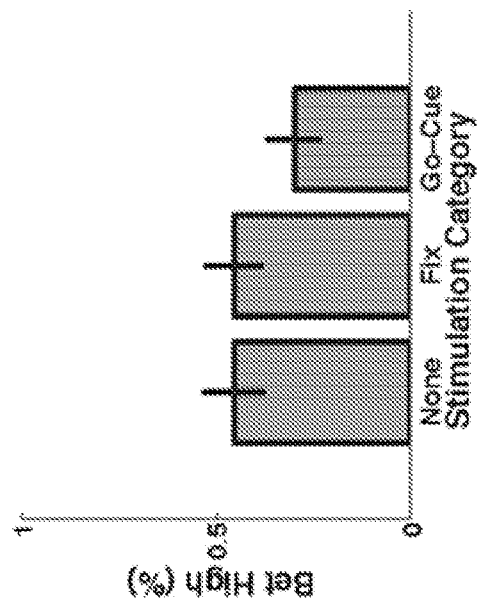
FIG. 11C is a graph illustrating a percentage of high bets over various stimulation categories during the transdiagnostic assessment task of FIG. 11A.
Figure 11B:
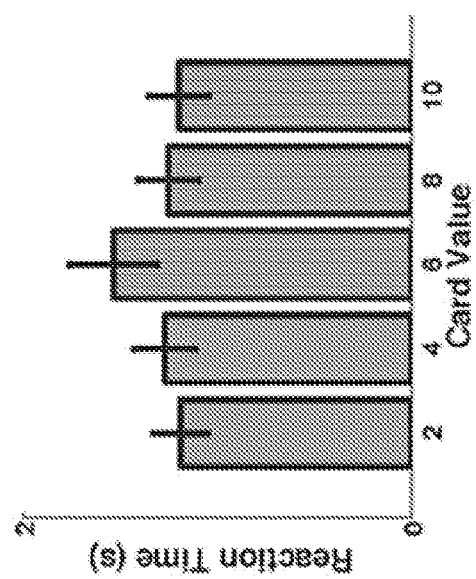
FIG. 11B is a graph illustrating a reaction time over various card values assessed during the transdiagnostic assessment task of FIG. 11A.

During the gambling task, the patient may be presented with a reduced 5-card deck of playing cards. The patient is instructed to play "war" against the computer and the patient bets whether their card is higher than the card displayed by the computer. There is an optimal bet for each card except 6. The 6 card, by definition, is a 50% win-lose chance, "decisional equipoise". As shown in FIG. 11B, the patients reaction time is greatest for the 6 card.

The gambling task may show that the example PTSD patient is unimpaired and/or impulsive. In other disorders, such as MDD, the gambling task may show loss aversion and generally slowed reaction times. GAD patients may show loss aversion and increased conservatism after a loss on a prior trial. TBI patients may show impulsivity and overall broad activations, and SUD patients may show impulsivity. BPD patients may show impulsive, suboptimal decision making, and pain patients may show a strong loss aversion, similar to MDD patients.

In one example, the system 10 may incorporate DBS to modify impulsive behavior, as indexed by the gambling task. For example, as shown in the graph of FIG. 11C, the STN brain region may be stimulated while the patient is betting, and the result shows a more conservative bet in comparison to no stimulation or fixed stimulation. The NAcc, VC-VS, and/or the OFC brain regions may also be stimulated to increase impulsivity. The subcortical brain region may also be stimulated to alter the impulsive-conservative balance. Additionally, or alternatively, the dACC brain region may be stimulated to slow processing, thereby forcing the patient to slow down and think before betting.

Figure 12A:
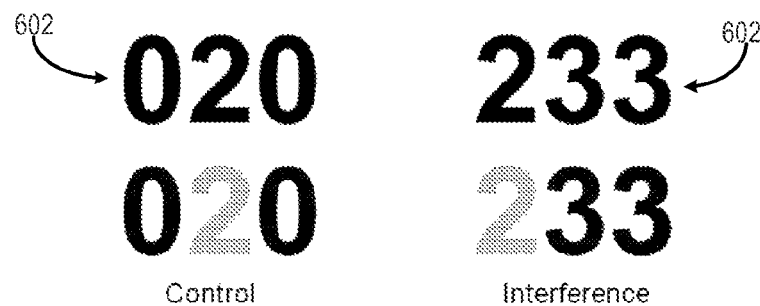
FIG. 12A is schematic illustration of an example transdiagnostic assessment task for measuring the functional domain of attention and perseveration.

Turning now to FIG. 12A, a multi-source interference task is shown for measuring the functional domain of flexibility and perseveration. Performance on this task assesses reaction time and measures cognitive capacity and cognitive flexibility. The multi-source interference task may be impaired for the example PTSD patient described above.

During the multi-source interference task, the patient may be provided a group of numbers 602 and asked to select one number from the group of numbers 602 that is different from the others. The patient may be asked to perform the multi-source interference task as quickly and accurately as possible. In general, interference stimuli should increase the patient's reaction time and switching rapidly between interference/non-interference trials may impose extra load. Further, having the patient perform the multi-source interference task alongside other emotional tasks, allows the system 10 to dissociate out the different effects and their networks.

The multi-source interference task may show that reaction times for the example PTSD patient is slowed under load. In other disorders, such as MDD and pain, the multi-source interference task may show greater interference effects and/or wider activation under interference. Similar to PTSD, a GAD patient and BPD patient may show slowed reaction times under load. TBI patients, and some SUD patients, may show poor trial-trial adaptation and greater interference effects due to dACC and/or dlPFC impairment, for example.

Figure 12B:
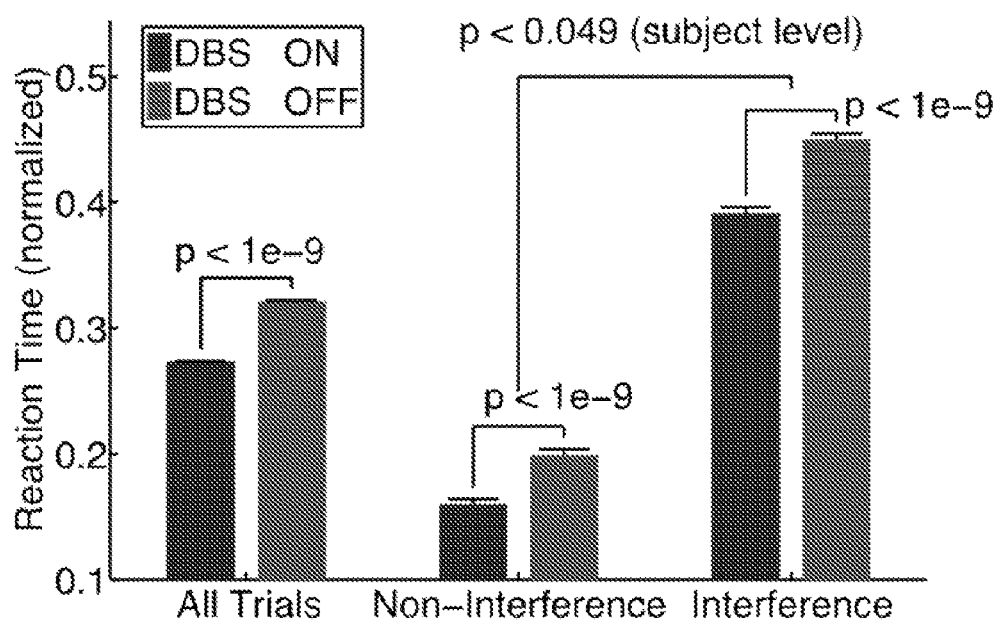
FIG. 12B is a graph illustrating a normalized reaction time over various trails including DBS stimulation during the transdiagnostic assessment task of FIG. 12A.

In one example, the system 10 may incorporate DBS to modify attention and perseveration behavior. As shown in FIG. 12B, the VC/VS brain region is chronically stimulated, but the DBS is turned off while the patient performs a multi-source interference task. As shown in the graph, the patient's reaction time is less when DBS is on, whereas the reaction time is longer under cognitive load from interference. That is, effective tuning of the DBS may modify the patient's reaction time, representing improvements in attention and mental flexibility. The system 10 may monitor responses in the dlPFC and dACC brain regions and tune VC-VS stimulation to keep overall activation adequate. In addition, frequency-domain signatures may be uncovered in processing of acquired data and serve as calibration to dissociate non-affect signals that should not be closed-loop targets.

Figure 13A:
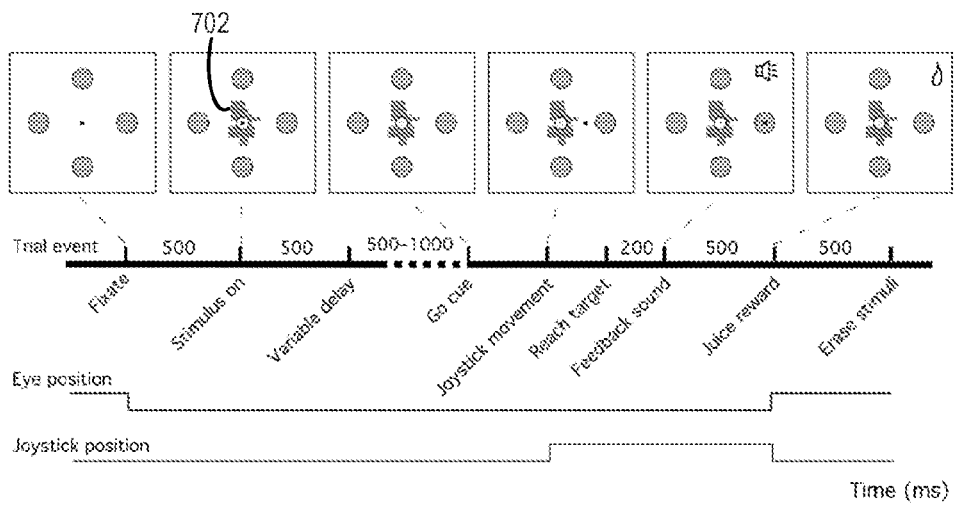
FIG. 13A is a schematic illustration of an example transdiagnostic assessment task for measuring the functional domain of cognitive capacity.

Turning now to FIG. 13A, an associative learning task is shown for measuring the functional domain of cognitive capacity. Performance on this task assesses the patient's speed to learn new items, memory, number of items that the patient can perform correctly at some criterion (e.g., 80% consistent correct), speed to detect a reversal when it happens (i.e., to notice that what was correct is now wrong), and perseverative thinking. The associative learning task may be impaired for the example PTSD patient described above.

During the associative learning task, the patient may be presented with a stimuli 702, such as a colored shape, and be instructed to move a joystick (not shown) to the right, for example, when presented with the stimuli. Thus, when the patient sees the stimuli 702, he/she should learn stimulus-response associations. The speed of learning associations and the number of associations that the patient can learn correctly may be a measure of the patient's overall cognitive capacity. Overall cognitive capacity may also be measured by adding rule-switching or reversals into the associative learning task. For example, after the patient learns a rule associated with the stimulus, the rule may suddenly change. Rule-switching or reversals may also be a measure of cognitive flexibility, top-down attention shifting, and frustration tolerance, which is often impaired in psychiatric disorders. The associative learning task also provides situations with prepotent and overlearned responses, the inhibition of which is a core psychiatric function.

The associative learning task may show that the example PTSD patient is characterized by extinction/reversal specific deficits. MDD patients may show more difficulty with set shifting, even when cued. Similar to PTSD, the associative learning task may show that a GAD patient shows extinction/reversal specific deficits. TBI patients may show perseveration on uncued or cued reversals and may also be impaired on association generally. SUD patients may show possible general impairment during the associative learning task, and BPD may show extinctions, reversals, and decreased capacity overall. Pain patients may show impaired set-shifting and reversals during the associative learning task.

In one example, the system 10 may incorporate DBS to modify associative learning behavior. For example, the NAcc, caudate, STN, OFC and/or the hippocampus brain region may be stimulated to modify the patient's ability to learn. Stimulation may be performed during a specific time-limited formal therapy or exposure sessions, and biomarkers (e.g., heart rate, skin conductance, etc.) may be incorporated to enhance safety/extinction learning.

Figure 13B:
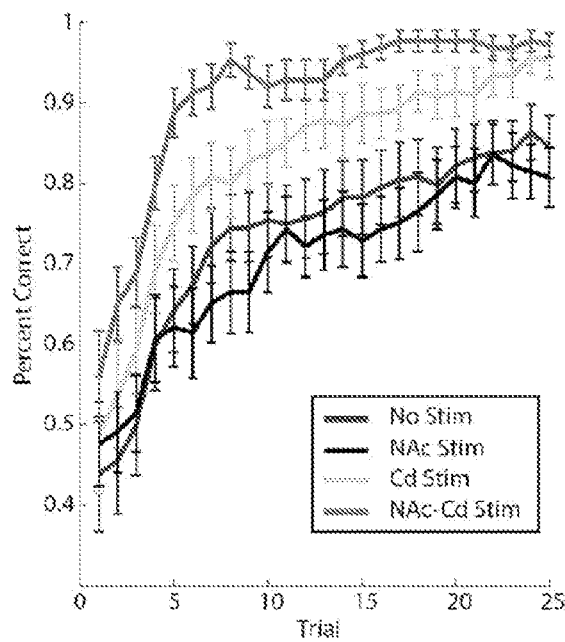
FIG. 13B is a graph illustrating a percentage of correct trials for patients receiving DBS stimulation in various brain regions over several trials while performing the transdiagnostic assessment task of FIG. 13A.

Turning now to FIG. 13B, cumulative data is shown from over 20 sessions in animals performing an associative learning task utilizing DBS stimulation in the Cd and NAc brain regions. Closed-loop stimulation may be applied in different combinations. For example, the best performance is shown when the subject received combined stimulation of the NAc and Cd brain regions. Thus, as shown in the graph of FIG. 13B, DBS stimulation at correct sites and timing may enhance learning and showing an improvement in overall performance approaching 100% correct.

Returning to FIG. 6, one or more of the psycho-physical tasks just described may be given to the patient while administering the transdiagnostic assessment at process block 202 in order to determine the patient's impairment along a set of functional domains. Once the transdiagnostic assessment is administered, the system 10 may record electrical, magnetic, or other physiologically produced activity from the patient's brain and/or body at process block 204 while the patient is performing one or more of the psycho-physical tasks. The activity may be recorded through non-invasive or invasive methodologies.

More specifically, at process block 204, while the patient is performing the task(s) of transdiagnostic assessment, multiple forms of electro-magnetic signals may be recorded from the patient during a single session, for example, or during multiple sessions of multiple modalities (i.e., imaging types) done over several days. In some embodiments, the majority of the electro-magnetic signals are measured from the patient's brain using one or more of structural magnetic resonance imaging (MRI), with particular variants such as diffusion tensor imaging (DTI), functional magnetic resonance imaging (fMRI), positron emission tomography (PET), single-photon emission computed tomography (SPECT), electroencephalography (EEG), magnetoencephalography (MEG), near-infrared spectroscopy (N IRS), reflected ultrasonic energy, fluorescent energy emitted from molecules within certain structures, direct recording of the brain with invasive, surgically implanted electrodes, and the like. Alternatively, any suitable method or combination of methods for recording the electro-magnetic signals of the brain with sufficient spatial resolution and temporal resolution may be used.

In some embodiments, the electrical activity recorded from the body at process block 204 may be accomplished by recording one or more biomarkers. These may be signals that relate to brain activity and psychological state, but are not directly measured from the brain. For example, the biomarkers may include, but are not limited to, heart rate, eye movements and blinks, eye pupil diameter, skin conductance/galvanic skin response (i.e., measure of autonomic arousal), respiratory rate, recorded speech (e.g., quantitatively analyzed for tone, amount, and prosody), and electromyography.

Once activity from the brain and body are recorded at process block 204, optionally, the system 10 may identify the patient's deviation in functional domains, such as the functional domains shown in the table of FIG. 7, that the transdiagnostic assessment showed as compared to healthy controls or population norms at process block 206. Transdiagnostic assessments of population norms may be acquired from a database of patients without evident psychiatric impairment who have performed the various transdiagnostic tasks. The patient's performance on the battery of transdiagnostic tasks may be compared to healthy controls by the system 10, or alternatively a trained clinician. As previously described, performance varies from task to task and may include, for example, how a biomarker changed in response to certain stimuli, how fast the patient responded to questions, what decisions the patient made when confronted with uncertain choices, and the like.

In one non-limiting example, the example PTSD patient may show impairment in the functional domains of fear extinction and a partial deficit in emotion regulation. However, the patient may not show impairment in the functional domains of cognitive capacity or reward motivation, whereas the patient may or may not show impairment in the decision making/impulsivity functional domain.

Figure 14:
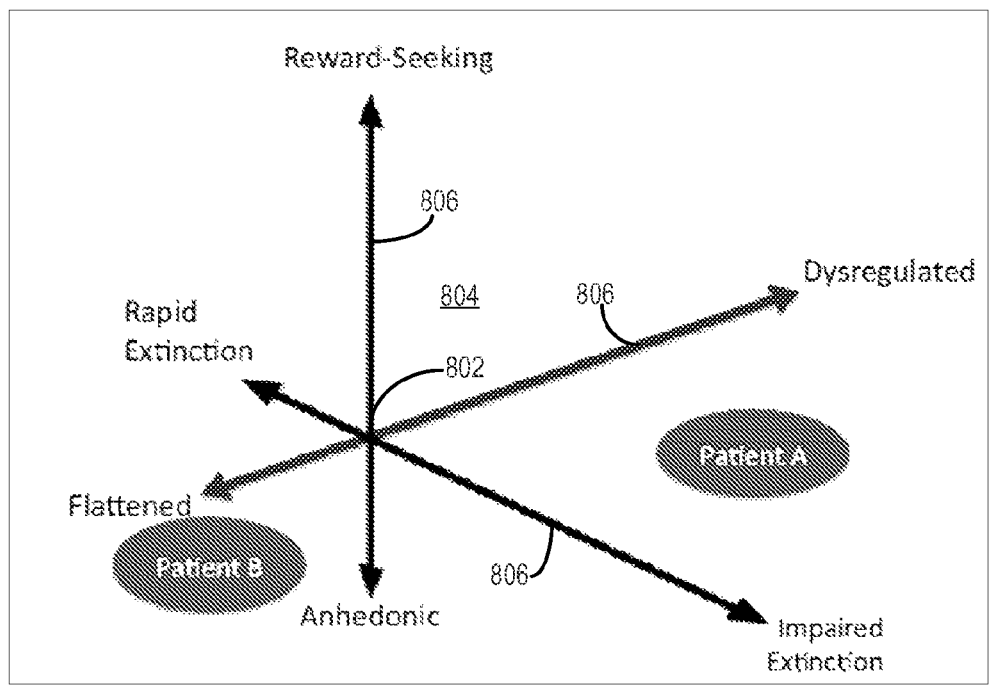
FIG. 14 is a schematic illustration of an analysis and interpretation of a transdiagnostic assessment for two patients within a transdiagnostic dimensional space.

As shown in FIG. 14, analysis and interpretation of a transdiagnostic assessment may classify patients by a distance from an origin 802. The origin 802 represents the population mean of healthy controls in a transdiagnostic space 804, which generally is high-dimensional. Scaling of the transdiagnostic space may be spherical, normalized by Z-scores, or allowed to remain elliptical. The degree of impairment along each axis 806 (i.e., the distance from the origin 802) may then prioritize the patient's treatment in terms of selecting brain stimulation locations and treatment modalities, as will be described in further detail below.

The example PTSD patient, shown in FIG. 14 as Patient A, may have a phenotype characterized by problems with excessive anxiety and deficient safety learning and is impaired in fear extinction and emotion regulation in the transdiagnostic space. However, Patient A is essentially at population normal for reward motivation. An alternate patient, Patient B shown in FIG. 14, may have depressive symptoms but less anxiety and shows over-regulated (i.e., flattened) emotion regulation and low reward motivation (i.e., anhedonia). However, Patient B may have no meaningful defect in fear extinction. Therefore, Patient A and Patient B can be classified differently in the transdiagnostic space 804.

Returning to FIG. 6, once the patient's deviation(s) in functional domains is identified at process block 206, the system 10 may identify the brain regions and signal characteristics within those brain regions that correspond to the patient's deviation from functional domains at process block 208. More specifically, once the patient's functional domains of maximal impairment have been identified, brain regions, as well as specific sub-regions within the brain regions, may be identified that correlate to that abnormality. This is done using the recordings of blocks 210 and 212, but may additionally involve consideration of general patterns of brain activation known to exist in the scientific literature.

In order to identify the brain regions and signal characteristics at process block 208, the brain imaging data acquired during the transdiagnostic assessment at process block 202 may be analyzed with relation to the patient's behavior on individual trials (stimulus presentations) of each behavioral task, starting with the most-impaired functional domains. The imaging data from the impaired functional domains may be compared to population averages to identify the brain regions where the patient has abnormally high or low levels of brain activity. Alternately, the population averages of other patients with similar behavioral performance may be substituted as a proxy for the individual patient's brain activity.

Figure 15:
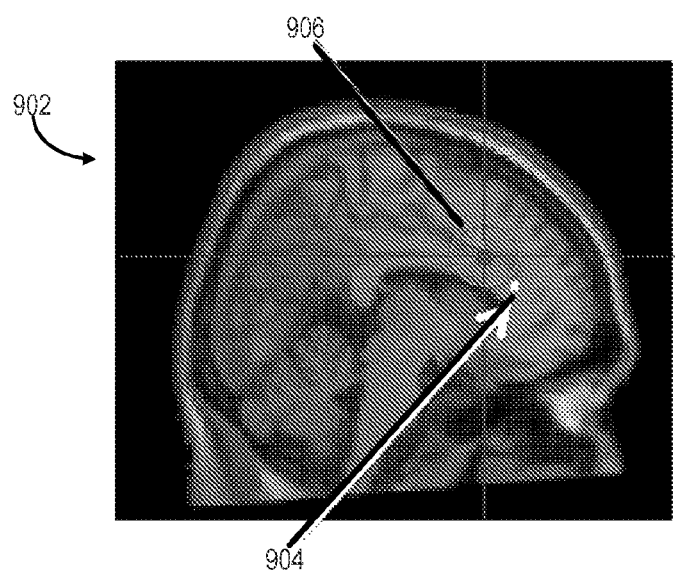
FIG. 15 is an image illustrating an example of patient-specific brain mapping relative to functional domains.

Furthermore, because the brain imaging data, such as brain imaging data 902 shown in FIG. 15, includes the patient's specific brain anatomy, the system 10 may identify one or more points 904 within the individual patient's brain that are generating the abnormal activity, as shown in FIG. 15. The point 904 of abnormal activity may be compared to a point 906 of normal activity as determined by behavior on a transdiagnostic task identified by a population average. In the example shown in FIG. 15, the individual patient with impairment on the task had a focus of maximum activation that was shifted by about 1 centimeter from the population average.

Once the brain regions related to the patient's impairment (i.e., deviations in functional domains) are identified at process block 208, additional imaging data of the brain regions may be obtained at process block 210 in order to identify abnormal features of neural activity. The additional imaging data may be acquired using any imaging modality having suitable high time resolution including, for example, EEG, MEG, invasive recording, EMG, and the like. Abnormal features of neural activity may include, for example, electrical signals from event-related potentials related to features of a transdiagnostic task, event-related synchronizations and de-synchronizations in the frequency domain related to task features, changes in phase of oscillatory brain activity (e.g., phase resetting), coupling and connectivity between different brain regions (e.g., coherence, phase-locking values, Granger causality, etc.), interactions of functional brain rhythms (cross-frequency coupling) within and between different structures, and the like.

Once the patient's impaired functional domain(s) have been identified and the brain regions and signals correlated to the impairment have been identified, the system 10 may apply stimulation to the identified brain regions at process block 212. In one example, stimulation may be performed with the electrodes 16 (see FIG. 1) having cortical and/or subcortical leads placed near brain regions of the patient. The stimulation may be applied to the brain regions identified at process block 208 in order to alter activity in those regions.

In some embodiments, sub-regions are selected within each brain region based on the imaging data obtained at process block 210. Stimulation modalities for applying stimulation to the identified brain regions and sub-regions at process block 212 may include, but are not limited to, non-invasive electro-magnetic modalities (e.g., transcranial magnetic stimulation, transcranial direct- or alternative-current stimulation, transcranial focused ultrasound, infra-red/optical through-skull modulation, etc.), invasive electro-magnetic modalities, and invasive optical modalities. In the case of invasive electro-magnetic modalities, electrodes or other amplifying devices may be surgically implanted into one or more brain regions and/or sub-regions. In the case of invasive optical modalities, transfection of one or more brain regions with proteins or other molecules may be involved that make neurons sensitive to light. Invasive optical modalities for stimulation may also involve implanting optical fibers into the brain regions. Combined non-invasive and invasive realizations, such as implantation of magnetic particles that then respond to applied magnetic fields, would also be reasonable.

Figure 16:
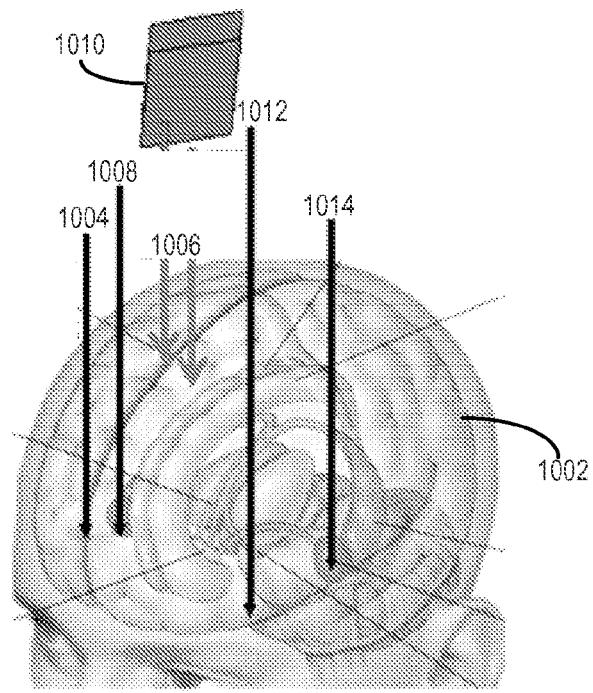
FIG. 16 is a schematic illustration of example implant sites for a patient with deficits in the functional domains of emotion regulation and fear extinction.

Turning to FIG. 16, the example PTSD patient's brain 1002 is shown with implant sites in various brain regions to modulate brain activity in the emotion regulation and fear extinction functional domains. The example PTSD patient with impaired fear extinction may have deficits localized in a first brain region 1004, such as the vmPFC, a second brain region 1006, such as the dACC, and a third brain region 1008, such as the amygdala. The vmPFC brain region 1004 and the amygdale 1008 are deep structures of the brain 1002, and the dACC brain region 1006 is superficial. Thus, brain activity may be modulated by placing electrodes surgically into any of the brain regions 1004, 1006, 1008, using a grid-type electrode 1010 for the superficial structure (i.e., the dACC brain region 1006) and deep brain stimulation probes 1012, 1014 for the vmPFC brain region 1004 and the amygdala brain region 1008, respectively.

Returning to FIG. 6, once stimulation is applied to the identified brain regions, the stimulation may be adjusted in real-time to suppress the identified abnormal signals within the target brain regions at process block 214. The stimulation may be directly adjusted using, for example, real-time recordings of brain electrical signals for closed loop control.

In one non-limiting example, if the patient receives an invasive stimulation modality including implanted electrodes, such as the electrodes 16 of system 10 shown in FIG. 2, and a neuro-stimulation pulse generator, such as the current pulse generator 54 shown in FIG. 2, to deliver electricity, stimulation may be delivered in a closed loop fashion. That is, the system may directly monitor the brain's electrical activity at the implant sites, and may alter the stimulation dose at each site based on observations throughout the network. In some embodiments, monitoring electrical activity may be done optically, for example, through genetically encoded voltage reporters. Monitoring may attempt to directly infer the patient's emotional state, to respond to the patient's intentional commands, or to merge both types of monitoring into a hybrid system.

In order to adequately adjust stimulation in the various brain regions at process block 214, an emotional decoding algorithm may be stored on the controlling hub 12 of system 10 (see FIG. 1) that can infer the patient's current emotional/symptom state from brain activity. The emotional decoding algorithm may utilize the time-resolved imaging and recording data acquired at process block 210. For example, it may be known that theta-frequency (4-8 Hz) coupling between the vmPFC brain region and the amygdala brain region plays a role in the encoding and extinction of fear memories. For the example PTSD patient, the emotional decoding algorithm may "decode" the patient's current capacity for fear extinction, either from relative theta power in the vmPFC and dACC brain regions, or more likely from theta-band coherence between the dACC, vmPFC, and amygdala brain regions.

In an alternative embodiment, the patient's overall level of fear may be focused on, and the amygdala activity (likely in the high-gamma 65-200 Hz band) may be monitored directly as a proxy for level of emotional distress. This could then be regulated with the help of an intention decoder, as will be described in further detail below. Regardless of the method used to adjust stimulation, there is a signal that the controller hub 12 (see FIG. 1) is programmed to sense. The controller hub 12 may then adjust stimulation (e.g., the stimulation intensity or different parameters) until the signal returns to a pre-defined range. For the example PTSD patient with impaired fear regulation, amygdala activity may be directly sensed, and the controller hub 12 may be configured to keep the amygdala activity within the pre-defined range (e.g., a pre-measured, non-anxious baseline). When amygdala activity exceeded the pre-defined range, the controller hub 12 may be configured to interpret this as the patient experiencing ungovernable fear, and would drive the implanted neurostimulator to shut down amygdala.

This closed-loop control may not be limited to brain electrical signals. For example, fear may be related to a number of autonomic signals that are detectable non-invasively, including heart rate variability, skin conductance, and pupil diameter. These autonomic signals may be measured by a non-invasive device, such as the sensors 58 shown in FIG. 2, and transmitted to the controller hub 12 via a communication protocol. The controller hub 12 may then integrate these peripheral biomarkers with its recorded neural signals to determine adequate stimulation adjustments to suppress the abnormal signals in the brain regions.

Once the stimulation is adjusted at process block 214, intentional control over the neurostimulation system (e.g., the BCI system 10) and how the closed-loop algorithm is applied may be provided to the patient at process block 216. By providing patient intentional control, difficulties with over-control and emotional numbing, for example, may be circumvented. The closed-loop controller may be an emotional/affective brain-computer interface (BCI), such as the BCI found in the system 10 of FIGS. 1 and 2, that actively monitors the patient's emotional experience as expressed in the patient's brain activity.

Figure 17:
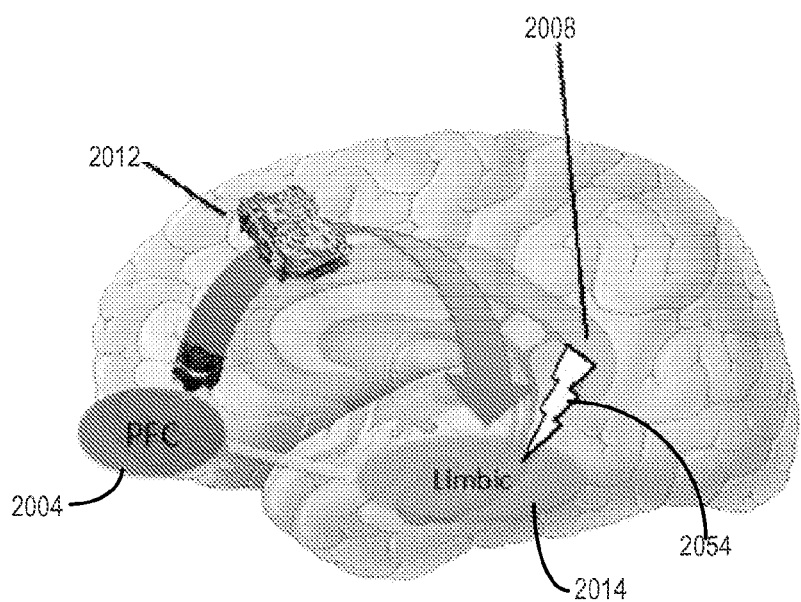
FIG. 17 is a schematic illustration of an example intention-decoding, BCI-based closed loop neurostimulator in accordance with the present invention.

Advantageously, the system 10 may have the ability to deploy the above described algorithms and have the algorithms available as the symptoms are experienced in the daily living of the patient. The patient may be given a degree of control over the stimulator's operation to gate its ability to turn stimulation on/off or to modulate the intensity. For example, FIG. 17 shows an example of a closed-loop affective decoder 2012 and brain stimulator 2054 for psychiatric indications. The affective decoder 2012 may be monitoring the vmPFC brain region 2004 and decoding the patient's intention to activate the stimulator 2054. The stimulator 2054 shown in FIG. 17 is operating in the limbic circuit 2014. The stimulator 2054 may be tracking and responding to activity in the amygdala brain region 2008. Command signals recorded in the vmPFC brain region 2004 may modulate the stimulator's 2054 behavior. When vmPFC activity is high, the stimulator 2054 may remain active and may be aggressive in emotional regulation. When vmPFC activity is low, the stimulator 2054 may allow amygdala activity to vary freely without intervening. Importantly, vmPFC activity is under the patient's direct and intentional control, meaning that the patient chooses what the stimulator 2054 will do.

More specifically, the system may use the patient's brain signals as a read-out of what he/she wants the stimulator to be doing, then use that to guide application of the closed-loop system. This may be called a hybrid BCI because there is an autonomous part (e.g., the emotional decoder) and a patient-controllable part (the intention decoder), and the two are coupled together to achieve adequate clinical performance. In some realizations, the emotional decoder may not be needed, or may be relatively trivial (e.g., the monitoring of a single channel in a single brain area).

Example

The prefrontal cortex may be a natural source of intentional emotion regulation signals, and therefore the BCI controller may not only infer the patient's emotional state, but may also decode volitionally controlled brain signals. The desire to suppress or amplify emotional experiences is already contained in PFC activity, and that activity may correlate directly with patients' ability to succeed in emotion regulation. Further, PFC neurons are flexible and may regularly re-tune themselves into new ensembles, encoding complex features of multiple tasks. Thus, given that plasticity may be important for successful affective decoding and control, a BCI that decodes signals from highly plastic cortex is more likely to succeed, because the brain can more readily re-tune to communicate a clinical need.

Unifying the themes above, one approach to affective BCI for closed-loop DBS is to record volitionally controlled signals from PFC, then use that activity as a reflection of the patient's desire to adjust stimulation parameters. This would not directly decode emotion, but instead could be seen as decoding an intention towards emotional regulation. That signal is well known to exist in PFC based on neuroimaging data. An affective decoder, similar to those already demonstrated, may then classify the patient's current emotional state and serve as a feedback signal for an adaptive stimulation algorithm. Alternatively, the volitional PFC activity could itself be that feedback signal. This 'direct control' BCI approach is known to be capable of decoding one or more degrees of freedom, which should be sufficient to control the parameters of most clinical brain stimulators. A rodent proof-of-concept study demonstrating this PFC-based affective BCI strategy is presented below, as well as how the strategy may be scaled and adapted to achieve the goal of closed-loop emotional brain stimulation. Importantly, although the examples below describe control based on the firing of single neurons, a wide range of signals may be used to encode and infer the patient's intention. This would include power in a variety of frequency bands, the connectivity between multiple brain areas, the summed firing of multiple neurons within one or more brain areas, and the like.

Figure 18A:
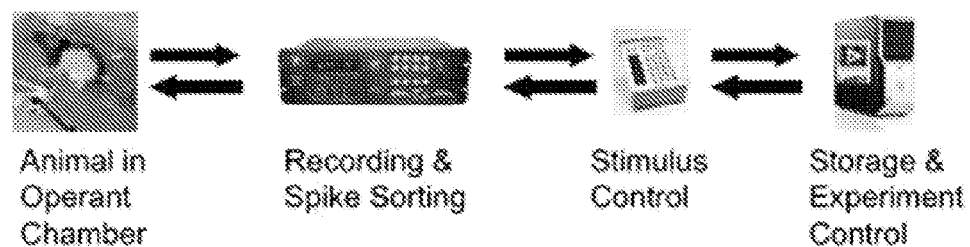
FIG. 18A is a block diagram illustrating an example tethered recording, decoding, and stimulating system in accordance with another aspect of the present invention.
Figure 18B:
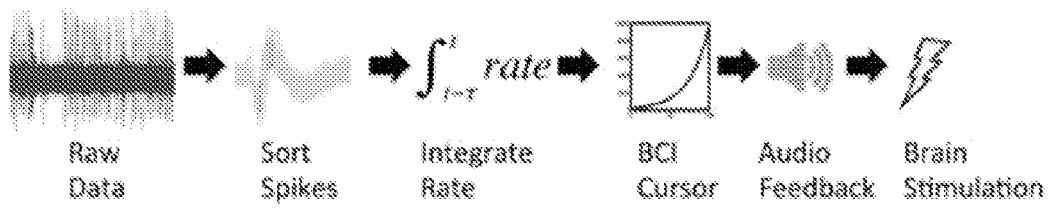
FIG. 18B is a schematic diagram illustrating a BCI algorithm to be incorporated into the system of FIG. 18A.

Turning to FIGS. 18A and 18B, a block diagram of an experimental setup and a schematic of an affective BCI algorithm are shown. The experimental setup of FIG. 18A includes a tethered recording, decoding, and stimulating system. Modular components control each function, permitting modification of experimental setup for alternate decoders or stimulation schemes. As illustrated, neural data flow from the animal in the operant chamber, through dedicated on-line spike sorting and behavioral tagging, to a desktop PC for processing and storage. Based on neural signals, the PC controls the behavioral system and stimulator, which deliver neurofeedback and brain stimulation to the animal.

Briefly, adult female Long-Evans rats were implanted with arrays of recording electrodes in the PFC (prelimbic and infralimbic cortices), and stimulating deep-brain electrodes. Stimulating electrodes targeted the medial forebrain bundle (MFB), a structure within the reward pathway where electrical stimulation is known to be reinforcing. MFB is a target for human clinical trials in DBS for depression, highlighting its relevance as a stimulation site in this closed-loop testbed. For this work, however, the MFB is used for its reinforcing properties, and not as a candidate treatment site for human translation.

Affective dysregulation and a desire to activate or alter brain stimulation can be decoded from volitionally controlled PFC activity. To demonstrate that rodents can learn to use an intention-decoding BCI to drive brain stimulation, the animals may be trained to use an auditory BCI. As shown in FIG. 18B, activity of a single unit recorded from the PFC may be converted to an auditory cursor using the BCI algorithm. Raw data may be recorded from the PFC and sorted online, after which spike rates may be estimated and converted to an audio cursor for the animal. The firing rate of the decoded unit may control the frequency of a tone presented to the animal, implementing a paradigm similar to a neurofeedback system. To model the plasticity component, the BCI was not trained or otherwise pre-tuned to neural firing modulation. Rather, at the start of each session a unit was selected and mapped into the BCI with fixed parameters. Animals were thus required to learn and adapt to the new BCI mapping each day to communicate their desire for neurostimulation.

Figure 18C:
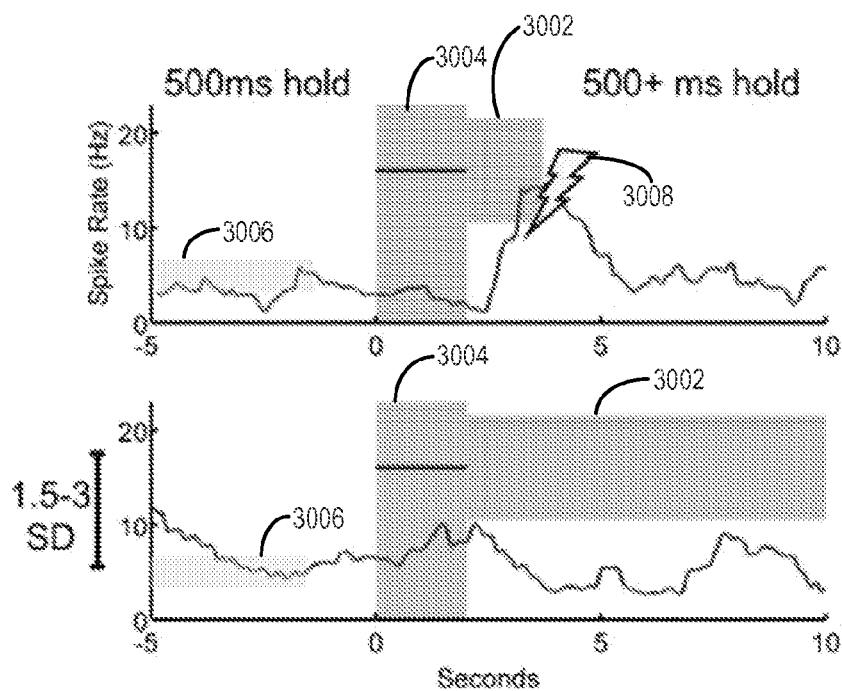
FIG. 18C is a graph illustrating a spike rate over time for successful use of the intentional control system compared to non-use of the intentional control system.

Referring to FIG. 18C, schematics of BCI trials are shown. The animal may be presented with auditory cues, represented as a target cue 3002 and corresponding cue periods 3004, initiated in a self-paced fashion by holding PFC activity at an initial baseline 3006. Moving the audio cursor to within a window of the target cue 3002 constituted control of the BCI, and activated neurostimulation in the medial forebrain bundle (MFB). Failure to reach the target cue 3002 within a pre-set time may have led to a brief time-out. In a human clinical system, subjects may deliberately avoid the target, and thus leave the neurostimulator off, except when the patient experiences symptoms that they wish to control. Because stimulation was reinforcing in this paradigm, the subject learned to use BCI to express desire for stimulation by acquiring targets when available and communicate an affect-regulation desire.

Baseline firing 3006 of the selected PFC unit was measured at the start of each day, and dwelling the firing rate at the baseline 3006 initiated a new trial. For each trial, a tone was briefly played, and the animal had 5-10 seconds to modulate the PFC firing rate to match her audio feedback cursor to the target cue 3002. Targets were based on the standard deviation (SD) of the baseline firing rate 3006, and required the animal to elevate firing rate by about 1.5 SD. Successful target acquisition, as shown in the top graph of FIG. 18C, triggered a phasic burst 3008 of MFB stimulation, whereas failure target acquisition, as shown in the bottom graph of FIG. 18C, did not. That is, each time the animal successfully controlled PFC neural firing, electrical stimulation was delivered within her limbic circuit. Trials were followed by brief time-outs, after which a new trial became available for self-initiation. This demonstrates the concept that volitional PFC activity can be decoded via a BCI and used as a signal of desire to activate a neurostimulator.

Figure 19:
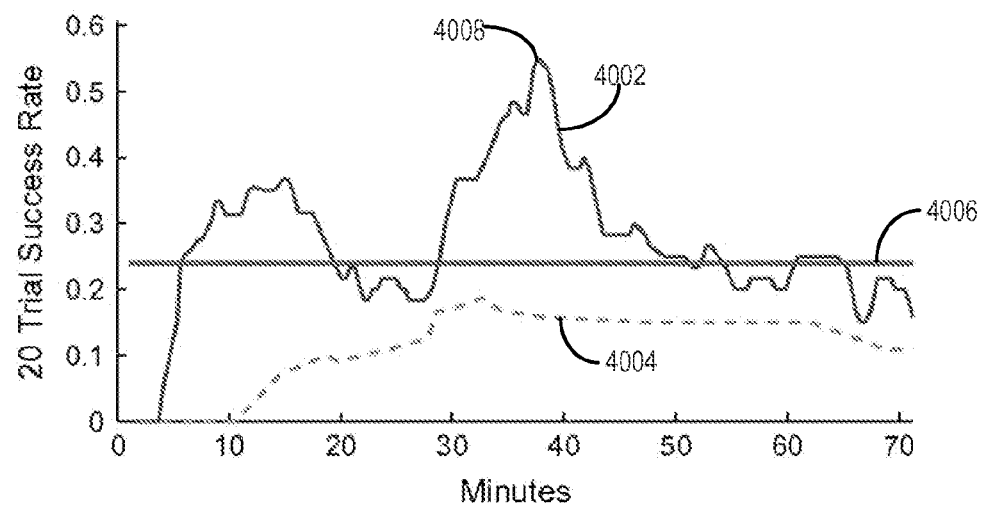
FIG. 19 is a graph illustrating success rates for BCI control over time for an actual target acquisition rate, an on-line estimate of chance-level performance, and an offline estimate of chance-level performance.

In the above described system, the animals successfully learned to control the PFC BCI to trigger MFB stimulation. For example, FIG. 19 shows successful PFC BCI control for limbic stimulation. A first line 4002 represents the actual target acquisition rate over a single testing session. A second dashed line 4004 and a horizontal solid line 4006 represent on-line ('catch') and off-line ('bootstrap') estimates of chance-level performance, respectively. BCI target acquisition, and thus successful delivery of reinforcing neurostimulation, rises to a peak 4008 above both measures of chance. Performance is sustained for over 20 minutes before the performance declines, possibly due to fatigue.

Target-acquisition rates were initially low as the animal learned the new decoder, then rapidly increased and were sustained for over 20 minutes, as just described. During this core performance period, when the animal had learned the decoder and was actively attending to the BCI, target hit rates remained well above both on-line (catch trials) 4004 and off-line (bootstrap replication) measures 4006 of chance. The animals generally learned to control newly isolated PFC units after about 20-40 minutes of practice. About eighty percent of tested sites in the PFC were controllable, consistent with the hypothesis that arbitrary neurons can be used for affective decoding by exploiting neuroplasticity.

Figure 20:
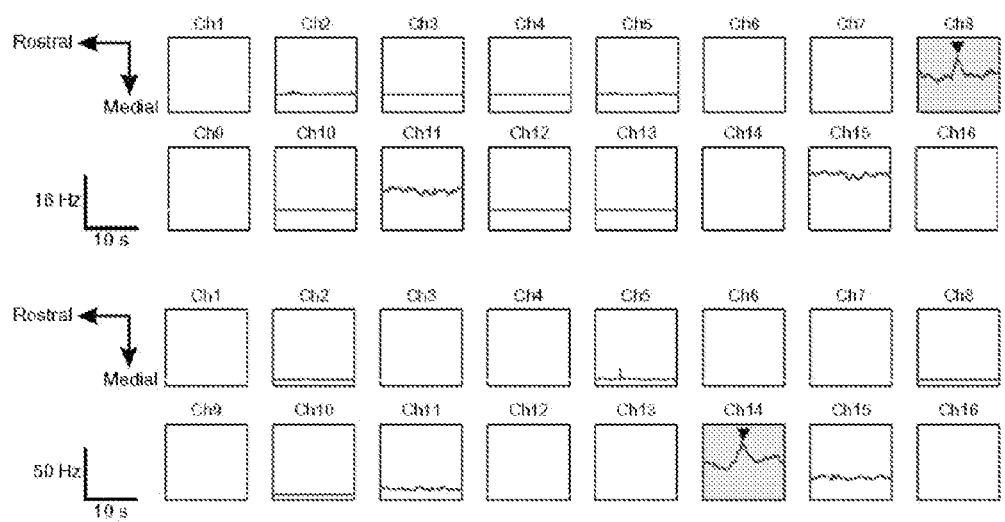
FIG. 20 is a schematic illustration of two examples of peri-stimulus discharge rates on single channels involved in the prefrontal cortex (PFC) BCI.

Referring to FIG. 20, control of PFC neurons in the BCI paradigm was highly specific. FIG. 20 shows two examples of peri-stimulus discharge rates on single channels involved in the PFC BCI. Examples are taken from the same animal, on two successive days, during which different units were controlled. Layout of subfigures within each example reflects relative location of individual electrodes within the cortex. In each panel, the channel controlling the BCI (A, channel 8; B, channel 14) shows a sharp rise into the middle of the target (arrowhead) followed by an equally sharp return to baseline once success is achieved. Other channels show little to no peri-event modulation, consistent with specific control of PFC unit selected for the BCI.

FIG. 20 further shows the averaged firing rates of multiple simultaneously recorded PFC units during two consecutive training days, time-locked to successful acquisition of a BCI target and delivery of reinforcing brain stimulation. Substantial modulation in discharge rate occurred on the channel used for the BCI (arrowhead). That channel, which was changed between these two sessions, shows a sharp rise into the target and equally sharp return to baseline after the onset of brain stimulation. The other, non-decoded channels show no average time-locked modulation. This provides further evidence that animals were able to specifically remap arbitrary PFC neurons to match the BCI decoder, establishing an 'emotional communication channel' to indicate their intent to receive neurostimulation. Intentional control of PFC units is also demonstrated by the channel-specific modulation of FIG. 20. This is evidence that animals were executing a learned and specific skill to achieve control of the BCI.

Psychiatric patients frequently report that they recognize emotional symptoms as 'not my real self' (ego-dystonic) and attempt to suppress them, clear evidence that they would be able to recognize the need to activate a stimulator. Some are even able to learn new cognitive skills that enable active suppression of symptoms. A responsive BCI based stimulator, such at the one just described, may effectively amplify those skills and achieve what some patients are unable to do on their own.

Work using similar operant paradigms has shown that artificial coupling of activity between two brain sites or between brain and spinal cord can induce long-term increases in functional connectivity. A hybrid BCI such as that described above could be targeted not to directly control symptoms, but to train and strengthen the user's internal regulatory circuits. This device would then be used for a limited time period to repair an identified brain deficit.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for diagnosing mental or emotional disorders comprising:
   a) administering, using a computer interface, a transdiagnostic assessment to a patient, the transdiagnostic assessment including at least one psycho-physical task;
   b) receiving a series of input data related to a brain of the patient acquired while the patient performs the at least one psycho-physical task;
   c) determining an impairment corresponding to the patient along a set of functional domains;
   d) recording, using a signal recorder, at least one of electrical, magnetic, optical, bio-acoustic, brain derived or body derived activity from the patient;
   e) identifying, from the at least one psycho-physical task, a deviation in the set of functional domains as compared to a predetermined control that indicates a mental or emotional disorder;
   f) identifying brain regions and signal characteristics corresponding to the identified deviation, using the input data;
   g) applying, using at least one stimulation device, stimulation to the identified brain regions to alter the at least one of electrical, magnetic, optical, bio-acoustic, brain derived or body derived activity in the brain regions; and
   wherein the functional domains include at least one of fear, reward motivation, emotion regulation, decision making/impulsivity, or attention/preservation.

2. The method of claim 1, wherein the at least one psycho-physical task is designed to probe functioning in at least one brain region of the patient.

3. The method of claim 1, wherein the series of input data includes at least one of electrical activity, magnetic activity, acoustic activity or medical images related to the brain of the patient.

4. The method of claim 1, wherein identifying brain regions and signal characteristics corresponding to the identified deviation further includes using general trends in the activity known to a skilled user.

5. The method of claim 1, wherein the at least one stimulation device includes at least one of an invasive stimulation device or a non-invasive stimulation device.

6. The method of claim 1, further comprising the step of obtaining additional imaging data of at least one of the brain regions or additional body recordings to identify abnormal features of the brain derived activity.

7. The method of claim 6, wherein the abnormal features of the brain derived activity include at least one of electrical signals from event-related potentials related to features of the at least one psycho-physical task, event-related synchronizations and de-synchronizations in a frequency domain related to features of the at least one psycho-physical task, changes in phase of oscillatory brain activity, coupling and connectivity between different brain regions, or interactions of functional brain rhythms within and between the different brain regions.

8. The method of claim 1, further comprising the step of adjusting, using an emotional decoding algorithm stored on a controller, stimulation to suppress abnormal signals in the brain regions, wherein the stimulation is adjusted in real-time to suppress the identified abnormal signals within the brain regions.

9. The method of claim 1, wherein the functional domains further include cognitive capacity.

10. The method of claim 1, wherein the at least one psycho-physical task includes at least one of a fear extinction task, an aversion reward conflict task, an emotion conflict resolution task, a gambling task, a cognitive interference task, or an associative learning task.

11. The method of claim 1, wherein the signal recorder includes at least one of structural magnetic resonance imaging (MRI), functional magnetic resonance imaging (fMRI), positron emission tomography (PET), single-photon emission computed tomography (SPECT), electroencephalography (EEG), magnetoencephalography (MEG), near-infrared spectroscopy (NIRS), ultrasound, fluorescent emission, or surgically implanted electrodes to measure the at least one of electrical, magnetic, bio-acoustic, brain derived or body derived activity.

12. The method of claim 1, wherein recording the at least one of electrical, magnetic, bio-acoustic, brain derived or body derived activity from the patient is accomplished by recording at least one biomarker.

13. The method of claim 12, wherein the at least one biomarker includes at least one of heart rate, eye movements, blinks, eye pupil diameter, skin conductance, galvanic skin response, respiratory rate, recorded speech, or electromyography.

14. The method of claim 1, further comprising the step of acquiring, from a database of patients without evident psychiatric impairment, transdiagnostic assessments to determine the predetermined control.

15. A system for diagnosing mental or emotional disorders comprising:
a computer interface for administering a transdiagnostic assessment to a patient, the transdiagnostic assessment including at least one psycho-physical task;
an acquisition device for acquiring a series of input data related to a brain of the patient while the patient performs the at least one psycho-physical task to determine an impairment corresponding to the patient along a set of functional domains;
a signal recorder for recording at least one of electrical, magnetic, bio-acoustic, brain derived or body derived activity from the patient;
a processor coupled to the computer interface and configured to identify, from the at least one psycho-physical task, a deviation from the set of functional domains as compared to a predetermined control that indicates a mental or emotional disorder, and identify brain regions and signal characteristics from the input data corresponding to the identified deviation;
at least one stimulation device for applying stimulation to the identified brain regions to alter the at least one of electrical, magnetic, bio-acoustic, brain derived or body derived activity in the brain regions; and
wherein the functional domains include at least one of fear, reward motivation, emotion regulation, decision making/impulsivity, or attention/preservation.

16. The system of claim 15, wherein the series of input data includes at least one of electrical activity, magnetic activity, acoustic activity or medical images related to the brain of the patient.

17. The system of claim 15, wherein the processor is further configured to identify brain regions and signal characteristics corresponding to the identified deviation using general trends in the activity known to a user.

18. The system of claim 15, wherein the at least one stimulation device includes at least one of an invasive stimulation device or a non-invasive stimulation device.

19. The system of claim 15, wherein the at least one psycho-physical task is designed to probe functioning in at least one brain region of the patient.

20. The system of claim 15, further including an emotional decoding algorithm stored on a controller for adjusting stimulation to suppress abnormal signals in the brain regions, wherein the stimulation is adjusted in real-time to suppress the identified abnormal signals within the brain regions.

21. The system of claim 15, wherein the functional domains further include cognitive capacity.

22. The system of claim 15, wherein the at least one psycho-physical task includes at least one of a fear extinction task, an aversion reward conflict task, an emotion conflict resolution task, a gambling task, a cognitive interference task, or an associative learning task.

23. The system of claim 15, wherein the signal recorder includes at least one of structural magnetic resonance imaging (MRI), functional magnetic resonance imaging (fMRI), positron emission tomography (PET), single-photon emission computed tomography (SPECT), electroencephalography (EEG), magnetoencephalography (MEG), near-infrared spectroscopy (NIRS), ultrasound, fluorescent emissions, or surgically implanted electrodes to measure the electrical activity.

24. The system of claim 15, wherein the signal recorder is configured to record electrical activity from the patient by recording at least one biomarker.

25. The system of claim 24, wherein the at least one biomarker includes at least one of heart rate, eye movements, blinks, eye pupil diameter, skin conductance, galvanic skin response, respiratory rate, recorded speech, or electromyography.

26. The system of claim 15, further comprising a database of patients without evident psychiatric impairment accessible by the processor to acquire transdiagnostic assessments to determine the predetermined control.

\* \* \* \* \*